(12) United States Patent
Pahl et al.

(10) Patent No.: US 9,695,480 B2
(45) Date of Patent: Jul. 4, 2017

(54) METHOD FOR THE DIAGNOSIS OF MYELOID NEOPLASIAS AND SOLID TUMORS

(71) Applicant: Universitaetsklinikum Freiburg, Freiburg (DE)

(72) Inventors: Heike Pahl, Freiburg (DE); Jonas Jutzi, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 14/377,468

(22) PCT Filed: Feb. 7, 2013

(86) PCT No.: PCT/EP2013/052361
§ 371 (c)(1),
(2) Date: Aug. 7, 2014

(87) PCT Pub. No.: WO2013/117609
PCT Pub. Date: Aug. 15, 2013

(65) Prior Publication Data
US 2015/0017642 A1    Jan. 15, 2015

(30) Foreign Application Priority Data
Feb. 8, 2012 (EP) .................................... 12154405

(51) Int. Cl.
| C12Q 1/68 | (2006.01) |
| C07H 21/02 | (2006.01) |
| C07H 21/04 | (2006.01) |

(52) U.S. Cl.
CPC ..... C12Q 1/6886 (2013.01); C12Q 2600/156 (2013.01)

(58) Field of Classification Search
None
See application file for complete search history.

(56) References Cited

U.S. PATENT DOCUMENTS

| 2002/0197611 A1 | 12/2002 | Chagovetz |
| 2005/0118625 A1 | 6/2005 | Mounts |
| 2009/0053752 A1 | 2/2009 | Blackman et al. |
| 2011/0104680 A1 | 5/2011 | Chinnaiyan et al. |

FOREIGN PATENT DOCUMENTS

| WO | WO 2005/085474 | 9/2005 |
| WO | WO 2008/060090 | 5/2008 |

OTHER PUBLICATIONS

NCBI Database (Bethesda, MD, USA) GenBank Accession No. DQ367844, Jan. 31, 2006.*
Catani et al . Leukemia. 2002. 16:1773-1781.*
Wang et al. Blood. 2010. 116(2):254-266.*
Pischedda et al (PNAS. 1995. 92: 3511-3515.*
Tamary et al. Eur J Haematol. 2003. 71: 196-203.*
Hirschhorn et al. (Genetics in Medicine. 2002. 4(2): 45-61.*
Hattersley et al. The Lancet. 2005. 366: 1315-1323.*
Wacholder et al J. Natl. Cancer Institute (2004) 96(6):434-442.*
Halushka et al. Nature. Jul. 1999. 22: 239-247.*
Gagneux et al. Molecular Phylogenetics and Evolution. 2001. 18: 2-13.*
Goto et al Cancer Epidemiol Biomarkers Prev. 2005. 14: 2454-2456.*
Randerson-Moor et al. J of Investigative Dermatology. 2004. 123: 755-759.*
Jutzi et al JEM. Apr. 15, 2013. 210:1003-1019.*
Catani et al Leukemia. 2002. 16: 1773-1781.*
Bean, T. et al., Nucl. Acids Res. (Jun. 15, 1997), vol. 25, No. 12, pp. 2509-2515.
Goerttler, Phillip et al., Brit. J. of Haem. (Apr. 1, 2005), vol. 129, No. 1, pp. 138-150.
Kaufmann, Kai et al., J. Exp. Med. (Jan. 16, 2012), vol. 209, No. 1, pp. 35-50.
Shivdasani, R. et al., Cell (Jun. 1, 1995), vol. 81, No. 5, pp. 695-704.
Tsutomu, Toki et al., Exp. Hema. (Oct. 1, 2000), vol. 28, No. 10, pp. 1113-1119.
Wang, W. et al., Blood (Jul. 15, 2010), vol. 116, No. 2, pp. 254-266.

\* cited by examiner

*Primary Examiner* — Carla Myers
(74) *Attorney, Agent, or Firm* — Chalin A. Smith; Smith Patent LLC

(57) ABSTRACT

The present application relates to an ex vivo or in vitro method to determine the presence or absence of a mutation or a variation in the NF-E2 gene in a sample from a patient suffering from a myeloid neoplasm or solid tumor whereby said method comprises:
a) obtaining a nucleic acid sample from the patient,
b) detecting the presence or absence of a mutation in the nucleic acid sample comprising the NF-E2 gene or a fragment thereof, characterized in that the presence of the mutation is an indication of a myeloid neoplasm or solid tumor, whereby the mutation is determined by comparing the nucleic acid sequence obtained from the sample with SEQ ID NO:1 or the complement thereof.

7 Claims, 20 Drawing Sheets

MSPCPPQQSRNRVIQLSTSELGEMELTWQEIMSITELQGLNAPSEPSFEPQ
APAPYLGPPPPTTYCPCSIHPDSGFPLPPPPYELPASTSHVPDPPYSYGNM
AIPVSKPLSLSGLLSEPLQDPLALLDIGLPAGPPKPQEDPESDSGLSLNYSD
AESLELEGTEAGRRRSEYVEMYPVEYPYSLMPNSLAHSNYTLPAAETPLAL
EPSSGPVRAKPTARGEAGSRDERRALAMKIPFPTDKIVNLPVDDFNELLAR
YPLTESQLALVRDIRRRGKNKVAAQNCRKRKLETIVQLERELERLTNERER
LLRARGEADRTLEVMRQQLTELYRDIFQHLRDESGNSYSPEEYALQQAAD
GTIFLVPRGTKMEATD

Figure 1

F-209 / Variant cDNA NM_006163 c.782-785delAGAG / Variant Protein:
p.E261AfsX3 / Protein ends at AA: 262 / Mutation in Exon 3

```
  1 GCATATACTGTCATCATCTTGGAAAGAAAAGGCTGAGAACGTAAAACTGAGGACAGAGGA
    ............................................................

61 GGAAAGCAGGGTGACCCCTGATGTTGCCCTAGAAAATGGAAAACAAAACACAGCAAAACA
    ............................................................

121 GAAAAACAGAAGATCTGACTCTGCCTTTAGCCAGGAAAACAGTTTGGGGGAGTAAAAAGT
    ............................................................

181 ATTACGGAAAAGAGTGGGCATTTTGCCTGGAAAAAAGGTTTCTAGAGCCATCTGGGCTTT
    ............................................................

241 CCGGGAACCTGGACCAGACTCTGGCCCAGTAGGATGTCCCCGTGTCCTCCCCAGCAGAGC
    ...........................................-M--S--P--C--P--P--Q--Q--S-

301 AGGAACAGGGTGATACAGCTGTCCACTTCAGAGCTAGGAGAGATGGAACTGACTTGGCAG
 10 -R--N--R--V--I--Q--L--S--T--S--E--L--G--E--M--E--L--T--W--Q-

361 GAGATCATGTCCATCACCGAGCTGCAGGGTCTGAATGCTCCAAGTGAGCCATCATTTGAG
 30 -E--I--M--S--I--T--E--L--Q--G--L--N--A--P--S--E--P--S--F--E-

421 CCCCAAGCCCCAGCTCCATACCTTGGACCTCCACCACCCACAACTTACTGCCCCTGCTCA
 50 -P--Q--A--P--A--P--Y--L--G--P--P--P--T--T--Y--C--P--C--S-

481 ATCCACCCAGATTCTGGCTTCCCACTTCCTCCACCACCTTATGAGCTCCCAGCATCCACA
 70 -I--H--P--D--S--G--F--P--L--P--P--P--Y--E--L--P--A--S--T-

541 TCCCATGTCCCAGATCCCCCATACTCCTATGGCAACATGGCCATACCAGTCTCCAAGCCA
 90 -S--H--V--P--D--P--P--Y--S--Y--G--N--M--A--I--P--V--S--K--P-

601 CTGAGCCTCTCAGGCCTGCTCAGTGAGCCGCTCCAAGACCCCTTAGCCCTCCTGGACATT
110 -L--S--L--S--G--L--L--S--E--P--L--Q--D--P--L--A--L--L--D--I-

661 GGGCTGCCAGCAGGGCCACCTAAGCCCCAAGAAGACCCAGAATCCGACTCAGGATTATCC
130 -G--L--P--A--G--P--P--K--P--Q--E--D--P--E--S--D--S--G--L--S-

721 CTCAACTATAGCGATGCTGAATCTCTTGAGCTGGAGGGGACAGAGGCTGGTCGGCGGCGC
150 -L--N--Y--S--D--A--E--S--L--E--L--E--G--T--E--A--G--R--R--R-

781 AGCGAATATGTAGAGATGTACCCAGTGGAGTACCCCTACTCACTCATGCCCAACTCCTTG
170 -S--E--Y--V--E--M--Y--P--V--E--Y--P--Y--S--L--M--P--N--S--L-

841 GCCCACTCCAACTATACCTTGCCAGCTGCTGAGACCCCCTTGGCCTTAGAGCCCTCCTCA
190 -A--H--S--N--Y--T--L--P--A--A--E--T--P--L--A--L--E--P--S--S-

901 GGCCCTGTGCGGGCTAAGCCCACTGCACGGGGGCAGGCAGGGAGTCGGGATGAACGTCGG
210 -G--P--V--R--A--K--P--T--A--R--G--E--A--G--S--R--D--E--R--R-

961 GCCTTGGCCATGAAGATTCCTTTTCCTACGGACAAGATTGTCAACTTGCCGGTAGATGAC
230 -A--L--A--M--K--I--P--F--P--T--D--K--I--V--N--L--P--V--D--D-

Del.
1021 TTTAATGAGCTATTGGCAAGGTACCCGCTGACA|AGAG|CC|AGC|TAG|CGCTAGTCCGGGAC
 250 -F--N--E--L--L--A--R--Y--P--L--T--|E--S|--Q--|L--|A--L--V--R--D-
                                         A    S   *
```

Figure 2

MPD-RC-241 / Variant cDNA NM_006163: c. 732_733insG / Variant Protein: p.L245VfsX5
/ Protein ends at AA: 248 / Mutation im Exon 3

```
  1 GCATATACTGTCATCATCTTGGAAAGAAAAGGCTGAGAACGTAAAACTGAGGACAGAGGA
    ............................................................

61 GGAAAGCAGGGTGACCCCTGATGTTGCCCTAGAAAATGGAAAACAAAACACAGCAAAACA
    ............................................................

121 GAAAAACAGAAGATCTGACTCTGCCTTTAGCCAGGAAAACAGTTTGGGGGAGTAAAAAGT
    ............................................................

181 ATTAGGGAAAAGAGTGGGCATTTTGCCTGGAAAAAAGGTTTCTAGAGCCATCTGGGCTTT
    ............................................................

241 CCGGGAACCTGGACCAGACTCTGGCCCAGTAGGATGTCCCCGTGTCCTCCCCAGCAGAGC
    .................................-M--S--P--C--P--P--Q--Q--S-

301 AGGAACAGGGTGATACAGCTGTCCACTTCAGAGCTAGGAGAGATGGAACTGACTTGGCAG
 10 -R--N--R--V--I--Q--L--S--T--S--E--L--G--E--M--E--L--T--W--Q-

361 GAGATCATGTCCATCACCGAGCTGCAGGGTCTGAATGCTCCAAGTGAGCCATCATTTGAG
 30 -E--I--M--S--I--T--E--L--Q--G--L--N--A--P--S--E--P--S--F--E-

421 CCCCAAGCCCCAGCTCCATACCTTGGACCTCCACCACCCACAACTTACTGCCCCTGCTCA
 50 -P--Q--A--P--A--P--Y--L--G--P--P--P--P--T--T--Y--C--P--C--S-

481 ATCCACCCAGATTCTGGCTTCCCACTTCCTCCACCACCTTATGAGCTCCCAGCATCCACA
 70 -I--H--P--D--S--G--F--P--L--P--P--P--P--Y--E--L--P--A--S--T-

541 TCCCATGTCCCAGATCCCCCATACTCCTATGGCAACATGGCCATACCAGTCTCCAAGCCA
 90 -S--H--V--P--D--P--P--Y--S--Y--G--N--M--A--I--P--V--S--K--P-

601 CTGAGCCTCTCAGGCCTGCTCAGTGAGCCGCTCCAAGACCCCTTAGCCCTCCTGGACATT
110 -L--S--L--S--G--L--L--S--E--P--L--Q--D--P--L--A--L--L--D--I-

661 GGGCTGCCAGCAGGGCCACCTAAGCCCCAAGAAGACCCAGAATCCGACTCAGGATTATCC
130 -G--L--P--A--G--P--P--K--P--Q--E--D--P--E--S--D--S--G--L--S-

721 CTCAACTATAGCGATGCTGAATCTCTTGAGCTGGAGGGGACAGAGGCTGGTCGGCGGCGC
150 -L--N--Y--S--D--A--E--S--L--E--L--E--G--T--E--A--G--R--R--R-

781 AGCGAATATGTAGAGATGTACCCAGTGGAGTACCCCTACTCACTCATGCCCAACTCCTTG
170 -S--E--Y--V--E--M--Y--P--V--E--Y--P--Y--S--L--M--P--N--S--L-

841 GCCCACTCCAACTATACCTTGCCAGCTGCTGAGACCCCCTTGGCCTTAGAGCCCTCCTCA
190 -A--H--S--N--Y--T--L--P--A--A--E--T--P--L--A--L--E--P--S--S-

901 GGCCCTGTGCGGGCTAAGCCCACTGCACGGGGGGAGGCAGGGAGTCGGGATGAACGTCGG
210 -G--P--V--R--A--K--P--T--A--R--G--E--A--G--S--R--D--E--R--R-
```

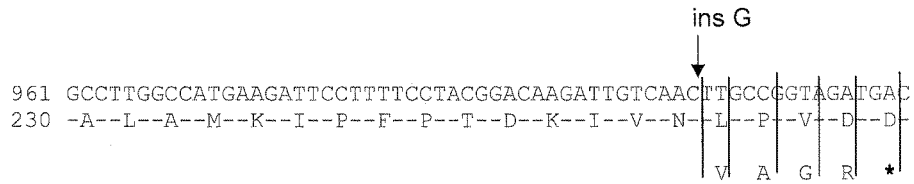

Figure 3

F-2836 und U-442 / Variant cDNA NM_006163: c.622insG / Variant Protein: pE221GfsX7 / Protein ends at AA: 227 / Mutation im Exon 3

```
  1 GCATATACTGTCATCATCTTGGAAAGAAAAGGCTGAGAACGTAAAACTGAGGACAGAGGA
    ............................................................

61 GGAAAGCAGGGTGACCCCTGATGTTGCCCTAGAAAATGGAAAACAAAACACAGCAAAACA
    ............................................................

121 GAAAAACAGAAGATCTGACTCTGCCTTTAGCCAGGAAAACAGTTTGGGGGAGTAAAAAGT
    ............................................................

181 ATTAGGGAAAAGAGTGGGCATTTTGCCTGGAAAAAAGGTTTCTAGAGCCATCTGGGCTTT
    ............................................................

241 CCGGGAACCTGGACCAGACTCTGGCCCAGTAGGATGTCCCCGTGTCCTCCCCAGCAGAGC
    .................................-M--S--P--C--P--P--Q--Q--S-

301 AGGAACAGGGTGATACAGCTGTCCACTTCAGAGCTAGGAGAGATGGAACTGACTTGGCAG
 10 -R--N--R--V--I--Q--L--S--T--S--E--L--G--E--M--E--L--T--W--Q-

361 GAGATCATGTCCATCACCGAGCTGCAGGGTCTGAATGCTCCAAGTGAGCCATCATTTGAG
 30 -E--I--M--S--I--T--E--L--Q--G--L--N--A--P--S--E--P--S--F--E-

421 CCCCAAGCCCCAGCTCCATACCTTGGACCTCCACCACCCACAACTTACTGCCCCTGCTCA
 50 -P--Q--A--P--A--P--Y--L--G--P--P--P--P--T--T--Y--C--P--C--S-

481 ATCCACCCAGATTCTGGCTTCCCACTTCCTCCACCACCTTATGAGCTCCCAGCATCCACA
 70 -I--H--P--D--S--G--F--P--L--P--P--P--Y--E--L--P--A--S--T-

541 TCCCATGTCCCAGATCCCCCATACTCCTATGGCAACATGGCCATACCAGTCTCCAAGCCA
 90 -S--H--V--P--D--P--P--Y--S--Y--G--N--M--A--I--P--V--S--K--P-

601 CTGAGCCTCTCAGGCCTGCTCAGTGAGCCGCTCCAAGACCCCTTAGCCCTCCTGGACATT
110 -L--S--L--S--G--L--L--S--E--P--L--Q--D--P--L--A--L--L--D--I-

661 GGGCTGCCAGCAGGGCCACCTAAGCCCCAAGAAGACCCAGAATCCGACTCAGGATTATCC
130 -G--L--P--A--G--P--P--K--P--Q--E--D--P--E--S--D--S--G--L--S-

721 CTCAACTATAGCGATGCTGAATCTCTTGAGCTGGAGGGGACAGAGGCTGGTCGGCGGCGC
150 -L--N--Y--S--D--A--E--S--L--E--L--E--G--T--E--A--G--R--R--R-

781 AGCGAATATGTAGAGATGTACCCAGTGGAGTACCCCTACTCACTCATGCCCAACTCCTTG
170 -S--E--Y--V--E--M--Y--P--V--E--Y--P--Y--S--L--M--P--N--S--L-

841 GCCCACTCCAACTATACCTTGCCAGCTGCTGAGACCCCCTTGGCCTTAGAGCCCTCCTCA
190 -A--H--S--N--Y--T--L--P--A--A--E--T--P--L--A--L--E--P--S--S-

G
                                          ↓
901 GGCCCTGTGCGGGCTAAGCCCACTGCACGGGG|GA|GG|CAGG|CAG|TCG|GA|TGA|ACGTCGG
210 -G--P--V--R--A--K--P--T--A--R--G-|-E-|-A-|-G-|-S-|-R-|-D-|-E-|-R--R-

|G |G |R |E |S |G |* |
```

Figure 4

U-532 / Variant cDNA NM_006163: c. 889_900del / Variant Protein: p.E297-R300del / Mutation im Exon 3

```
  1 GCATATACTGTCATCATCTTGGAAAGAAAAGGCTGAGAACGTAAAACTGAGGACAGAGGA
    ............................................................

61 GGAAAGCAGGGTGACCCCTGATGTTGCCCTAGAAAATGGAAAACAAAACACAGCAAAACA
    ............................................................

121 GAAAAACAGAAGATCTGACTCTGCCTTTAGCCAGGAAAACAGTTTGGGCGAGTAAAAAGT
    ............................................................

181 ATTAGGGAAAAGAGTGGGCATTTTGCCTGGAAAAAAGGTTTCTAGAGCCATCTGGGCTTT
    ............................................................

241 CCGGGAACCTGGACCAGACTCTGGGCCAGTAGGATGTCCCCGTGTCCTCCCCAGCAGAGC
    ...............................-M--S--P--C--P--P--Q--Q--S-

301 AGGAACAGGGTGATACAGCTGTCCACTTCAGAGCTAGGAGAGATGGAACTGACTTGGCAG
 10 -R--N--R--V--I--Q--L--S--T--S--E--L--G--E--M--E--L--T--W--Q-

361 GAGATCATGTCCATCACCGAGCTGCAGGGTCTGAATGCTCCAAGTGAGCCATCATTTGAG
 30 -E--I--M--S--I--T--E--L--Q--G--L--N--A--P--S--E--P--S--F--E-

421 CCCCAAGCCCCAGCTCCATACCTTGGACCTCCACCACCCACAACTTACTGCCCCTGCTCA
 50 -P--Q--A--P--A--P--Y--L--G--P--P--P--P--T--T--Y--C--P--C--S-

481 ATCCACCCAGATTCTGGCTTCCCACTTCCTCCACCACCTTATGAGCTCCCAGCATCCACA
 70 -I--H--P--D--S--G--F--P--L--P--P--P--P--Y--E--L--P--A--S--T-

541 TCCCATGTCCCAGATCCCCCATACTCCTATGGCAACATGGCCATACCAGTCTCCAAGCCA
 90 -S--H--V--P--D--P--P--Y--S--Y--G--N--M--A--I--P--V--S--K--P-

601 CTGAGCCTCTCAGGCCTGCTCAGTGAGCCGCTCCAAGACCCCTTAGCCCTCCTGGACATT
110 -L--S--L--S--G--L--L--S--E--P--L--Q--D--P--L--A--L--L--D--I-

661 GGGCTGCCAGCAGGGCCACCTAAGCCCCAAGAAGACCCAGAATCCGACTCAGGATTATCC
130 -G--L--P--A--G--P--P--K--P--Q--E--D--P--E--S--D--S--G--L--S-

721 CTCAACTATAGCGATGCTGAATCTCTTGAGCTGGAGGGGACAGAGGCTGGTCGGCGGCGC
150 -L--N--Y--S--D--A--E--S--L--E--L--E--G--T--E--A--G--R--R--R-

781 AGCGAATATGTAGAGATGTACCCAGTGGACTACCCCTACTCACTCATGCCCAACTCCTTG
170 -S--E--Y--V--E--M--Y--P--V--E--Y--P--Y--S--L--M--P--N--S--L-

841 GCCCACTCCAACTATACCTTGCCAGCTGCTGAGACCCCCTTGGCCTTAGAGCCCTCCTCA
190 -A--H--S--N--Y--T--L--P--A--A--E--T--P--L--A--L--E--P--S--S-

901 GGCCCTGTGCGGGCTAAGCCCACTGCACGGGGGGAGGCACGGAGTCGGGATGAACGTCGG
210 -G--P--V--R--A--K--P--T--A--R--G--E--A--G--S--R--D--E--R--R-

961 GCCTTGGCCATGAAGATTCCTTTTCCTACGGACAAGATTGTCAACTTGCCGGTAGATGAC
230 -A--L--A--M--K--I--P--F--P--T--D--K--I--V--N--L--P--V--D--D-

1021 TTTAATGAGCTATTGGCAAGGTACCCGCTGACAGAGAGCCAGCTAGCGCTAGTCCGGGAC
250 -F--N--E--L--L--A--R--Y--P--L--T--E--S--Q--L--A--L--V--R--D-
```

Figure 5A

```
1081 ATCCGACGACGGGGCAAAAACAAGGTGGCAGCCCAGAACTGCCGCAAGAGGAAGCTGGAA
 270 -I--R--R--R--G--K--N--K--V--A--A--Q--N--C--R--K--R--K--L--E-

1141 ACCATTGTGCAGCTGGAGCGGGAGCTGGAGCGGCTGACCAATGAACGGGAGCGGCTTCTC
 290 -T--I--V--Q--L--E--R--E--L--E--R--L--T--N--E--R--E--R--L--L-
                              Deletion 1201 AGGGCCCGCGGGGAGGCAGACCGGACCCTGGAGGTCATGCGCCAACAGCTGACAGAGCTG
 310 -R--A--R--G--E--A--D--R--T--L--E--V--M--R--Q--Q--L--T--E--L-

1261 TACCGTGACATTTTCCAGCACCTTCGGGATGAATCAGGCAACAGCTACTCTCCTGAAGAG
 330 -Y--R--D--I--F--Q--H--L--R--D--E--S--G--N--S--Y--S--P--E--E-

1321 TACGCGCTGCAACAGGCTGCCGATGGGACCATCTTCCTTGTGCCCCGGGGGACCAAGATG
 350 -Y--A--L--Q--Q--A--A--D--G--T--I--F--L--V--P--R--G--T--K--M-

1381 GAGGCCACAGACTGAGCTGGCCCAGAGGGGTGGAACTGCTGATGGGATTTCCTTCATTCC
 370 -E--A--T--D--*-..............................................

1441 CTTCTGATAAAGGTACTCCCCAACCCTGAGTCCCAGAAGGAGCTGAGTTCTCTAGACCAG
      ..............................................................

1501 AAGAGGATGACAATGGCAACAAGTGTTTGGAAGTTCCAAGGTGTCTTCAAAGAGGCTTGC
      ..............................................................

1561 CTTGAGGGAGGGCTGGAATCTGTCTTCCCTGACTCGGCTCCTCAGGTCTTTAGCCTCCAC
      ..............................................................

1621 CTTGTCTAAGCTTTGGTCTATAAAGTGCGCTACAGAAA
```

Figure 5 B

U-409 / Variant cDNA NM_006163: c. 236delC / Variant Protein: p.P79LfsX32 / Protein ends at AA: 109 / Mutation im Exon 3

```
  1 GCATATACTGTCATCATCTTGGAAAGAAAAGGCTGAGAACGTAAAACTGAGGACAGAGGA
    ............................................................

61 GGAAAGCAGGGTGACCCCTGATGTTGCCCTAGAAAATGGAAAACAAAACACAGCAAAACA
    ............................................................

121 GAAAAACAGAAGATCTGACTCTGCCTTTAGCCAGGAAAACAGTTTGGGGGAGTAAAAAGT
    ............................................................

181 ATTAGGGAAAAGAGTGGGCATTTTGCCTGGAAAAAAGGTTTCTAGAGCCATCTGGGCTTT
    ............................................................

241 CCGGGAACCTGGACCAGACTCTGGCCCAGTAGGATGTCCCCGTGTCCTCCCCAGCAGAGC
    .................................-M--S--P--C--P--P--Q--Q--S-

301 AGGAACAGGGTGATACAGCTGTCCACTTCAGAGCTAGGAGAGATGGAACTGACTTGGCAG
 10 -R--N--R--V--I--Q--L--S--T--S--E--L--G--E--M--E--L--T--W--Q-

361 GAGATCATGTCCATCACCGAGCTGCAGGGTCTGAATGCTCCAAGTGAGCCATCATTTGAG
 30 -E--I--M--S--I--T--E--L--Q--G--L--N--A--P--S--E--P--S--F--E-

421 CCCCAAGCCCCAGCTCCATACCTTGGACCTCCACCACCCACAACTTACTGCCCCTGCTCA
 50 -P--Q--A--P--A--P--Y--L--G--P--P--P--T--T--Y--C--P--C--S-
```

Del. C

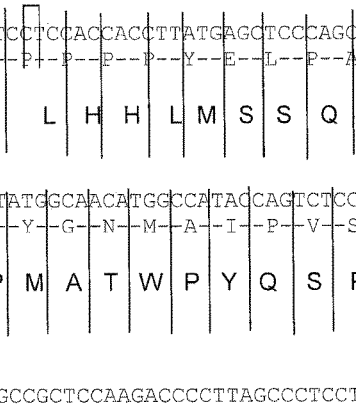

```
481 ATCCACCCAGATTCTGGCTTCCCACTTCCTCCACCACCTTATGAGCTCCAGCATCCACA
 70 -I--H--P--D--S--G--F--P--L--P--P--P--Y--E--L--P--A--S--T-
```

| L | H | H | L | M | S | S | Q | H | P | H |

```
541 TCCCATGTCCCAGATCCCCATACTCCTATGGCAACATGGCCATACCAGTCTCCAAGCCA
 90 -S--H--V--P--D--P--P--Y--S--Y--G--N--M--A--I--P--V--S--K--P-
```

| P | M | S | Q | I | P | H | T | P | M | A | T | W | P | Y | Q | S | P | S | H |

```
601 CTGAGCCTCTCAGGCCTGCTCAGTGAGCCGCTCCAAGACCCCTTAGCCCTCCTGGACATT
110 -L--S--L--S--G--L--L--S--E--P--L--Q--D--P--L--A--L--L--D--I-
      *
```

Figure 6

U-980 / Variant cDNA NM_006163: c. 780_781insA / Variant Protein: p.E261RfsX44 / Protein ends at AA: 304 / Mutation im Exon 3

```
      GCATATACTGTCATCATCTTGGAAAGAAAAGCCTGACAACGTAAAACTGAGGACAGAGGA
      ............................................................

61  GGAAAGCAGGGTGACCCCTGATGTTGCCCTAGAAAATGGAAAACAAAACACAGCAAAACA
      ............................................................

121  GAAAAACAGAAGATCTGACTCTGCCTTTAGCCAGGAAAACAGTTTGGGGGAGTAAAAAGT
      ............................................................

181  ATTAGGGAAAAGAGTGGGCATTTTGCCTGGAAAAAAGGTTTCTAGAGCCATCTGGGCTTT
      ............................................................

241  CCGGGAACCTGGACCAGACTCTGGCCCAGTAGGATGTCCCCGTGTCCTCCCCAGCAGAGC
      ...........................................-M--S--P--C--P--P--Q--S-

301  AGGAACAGGGTGATACAGCTGTCCACTTCAGAGCTAGGAGAGATGGAACTGACTTGGCAG
  10  -R--N--R--V--I--Q--L--S--T--S--E--L--G--E--M--E--L--T--W--Q-

361  GAGATCATGTCCATCACCGAGCTGCAGGGTCTGAATGCTCCAAGTGAGCCATCATTTGAG
  30  -E--I--M--S--I--T--E--L--Q--G--L--N--A--P--S--E--P--S--F--E-

421  CCCCAAGCCCCAGCTCCATACCTTGGACCTCCACCACCCACAACTTACTGCCCCTGCTCA
  50  -P--Q--A--P--A--P--Y--L--G--P--P--P--T--T--Y--C--P--C--S-

481  ATCCACCCAGATTCTGGCTTCCCACTTCCTCCACCACCTTATGAGCTCCAGCATCCACA
  70  -I--H--P--D--S--G--F--P--L--P--P--P--Y--E--L--P--A--S--T-

541  TCCCATGTCCCAGATCCCCCATACTCCTATGGCAACATGGCCATACCAGTCTCCAAGCCA
  90  -S--H--V--P--D--P--P--Y--S--Y--G--N--M--A--I--P--V--S--K--P-

601  CTGAGCCTCTCAGGCCTGCTCAGTGAGCCGCTCCAAGACCCCTTAGCCCTCCTGGACATT
 110  -L--S--L--S--G--L--L--S--E--P--L--Q--D--P--L--A--L--L--D--I-

661  GGGCTGCCAGCAGGGCCACCTAAGCCCCAAGAAGACCCAGAATCCGACTCAGGATTATCC
 130  -G--L--P--A--G--P--P--K--P--Q--E--D--P--E--S--D--S--G--L--S-

721  CTCAACTATAGCGATGCTGAATCTCTTGAGCTGGAGGGGACAGAGGCTGGTCGGCGGCGC
 150  -L--N--Y--S--D--A--E--S--L--E--L--E--G--T--E--A--G--R--R--R-

781  AGCGAATATGTAGAGATGTACCCAGTGGAGTACCCCTACTCACTCATGCCCAACTCCTTG
 170  -S--E--Y--V--E--M--Y--P--V--E--Y--P--Y--S--L--M--P--N--S--L-

841  GCCCACTCCAACTATACCTTGCCAGCTGCTGAGACCCCCTTGGCCTTAGAGCCCTCCTCA
 190  -A--H--S--N--Y--T--L--P--A--A--E--T--P--L--A--L--E--P--S--S-

901  GGCCCTGTGCGGGCTAAGCCCACTGCACGGGGGGAGGCAGGGAGTCGGGATGAACGTCGG
 210  -G--P--V--R--A--K--P--T--A--R--G--E--A--G--S--R--D--E--R--R-

961  GCCTTGGCCATGAAGATTCCTTTTCCTACGGACAAGATTGTCAACTTGCCGGTAGATGAC
 230  -A--L--A--M--K--I--P--F--P--T--D--K--I--V--N--L--P--V--D--D-
```

Figure 7A

```
                                    Ins A
                                      ↓
1021 TTTAATGAGCTATTGGCAAGGTACCCGCTGACAGAGAGCCAGCTAGCGCTAGTCCGGGAC
 250  -F---N---E---L---L---A---R---Y---P---L---T---E---S---Q---L---A---L---V---R---D-
                                       R   E   P  A   S  A   S  P  G

1081 ATCCGACGACGGGGCAAAAACAAGGTGGCAGCCCAGAACTGCCGCAAGAGCAAGCTGGAA
 270  -I---R---R---R---G---K---N---K---V---A---A---Q---N---C---R---K---R---K---L---E-
      H  P   T   T  G  Q  K  Q  G   G   S  P   E   L   P  Q  E   E  A   G

1141 ACCATTGTGCAGCTGGAGCGGGAGCTGGAGCGGCTGACCAATGAACGGGAGCGGCTTCTC
 290  -T---I---V---Q---L---E---R---E---L---E---R---L---T---N---E---R---E---R---L---L-
      N  H  C   A  A  G  A   G  A   G   A  A  D   Q    *
```

Figure 7 B

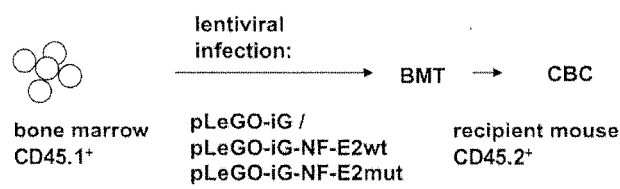
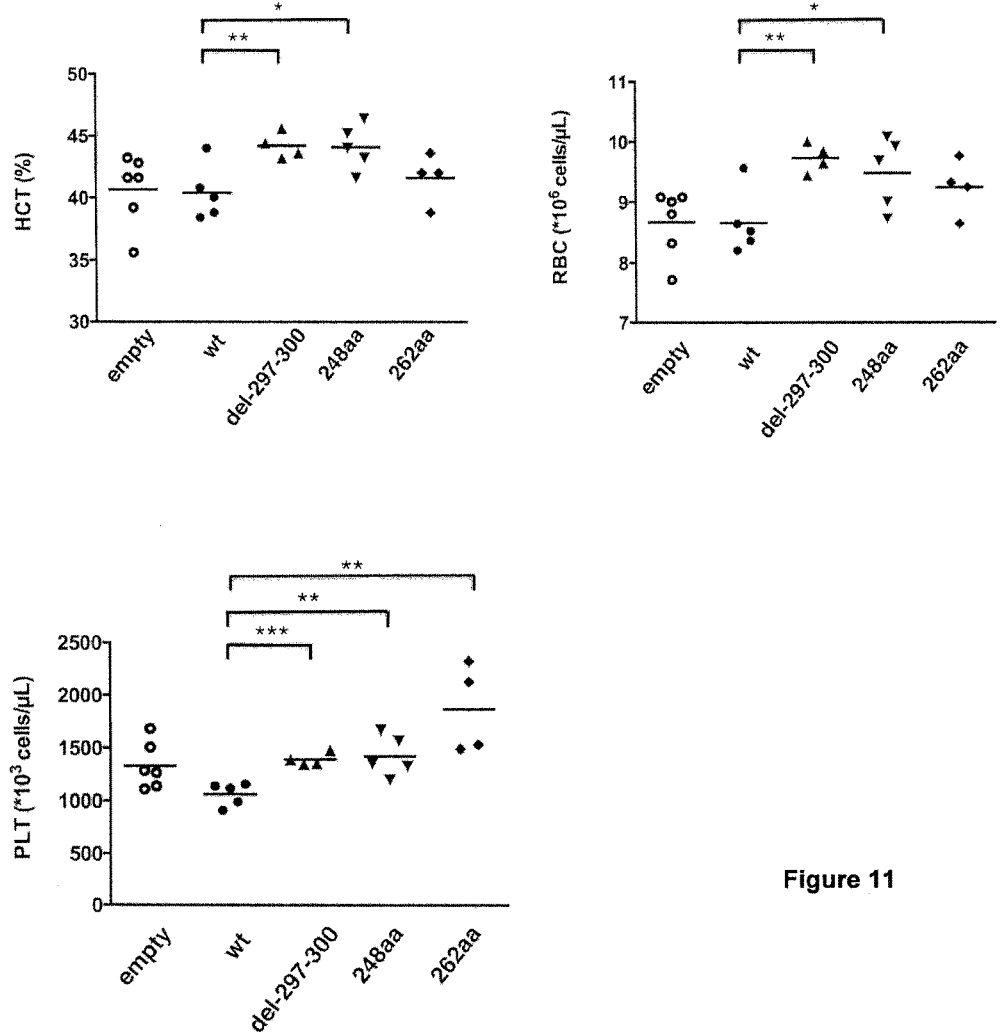
Figure 11

Figure 12 – Effect of NF-E2 on erythroid maturation

SEQUENCE LISTING

<160> NUMBER OF SEQ ID NOS: 25

<210> SEQ ID NO 1
<211> LENGTH: 373
<212> TYPE: PRT
<213> ORGANISM: Homo sapiens

<400> SEQUENCE: 1

```
Met Ser Pro Cys Pro Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
            35                  40                  45

Glu Pro Gln Ala Pro Ala Pro Tyr Leu Gly Pro Pro Pro Thr Thr
    50                  55                  60

Tyr Cys Pro Cys Ser Ile His Pro Asp Ser Gly Phe Pro Leu Pro Pro
65                  70                  75                  80

Pro Pro Tyr Glu Leu Pro Ala Ser Thr Ser His Val Pro Asp Pro Pro
            85                  90                  95

Tyr Ser Tyr Gly Asn Met Ala Ile Pro Val Ser Lys Pro Leu Ser Leu
            100                 105                 110

Ser Gly Leu Leu Ser Glu Pro Leu Gln Asp Pro Leu Ala Leu Leu Asp
            115                 120                 125

Ile Gly Leu Pro Ala Gly Pro Pro Lys Pro Gln Glu Asp Pro Glu Ser
130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Arg Ser Glu Tyr Val Glu Met Tyr
                165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
            195                 200                 205

Ser Gly Pro Val Arg Ala Lys Pro Thr Ala Arg Gly Glu Ala Gly Ser
            210                 215                 220

Arg Asp Glu Arg Arg Ala Leu Ala Met Lys Ile Pro Phe Pro Thr Asp
225                 230                 235                 240

Lys Ile Val Asn Leu Pro Val Asp Asp Phe Asn Glu Leu Leu Ala Arg
                245                 250                 255

Tyr Pro Leu Thr Glu Ser Gln Leu Ala Leu Val Arg Asp Ile Arg Arg
            260                 265                 270

Arg Gly Lys Asn Lys Val Ala Ala Gln Asn Cys Arg Lys Arg Lys Leu
            275                 280                 285

Glu Thr Ile Val Gln Leu Glu Arg Glu Leu Glu Arg Leu Thr Asn Glu
    290                 295                 300

Arg Glu Arg Leu Leu Arg Ala Arg Gly Glu Ala Asp Arg Thr Leu Glu
305                 310                 315                 320

Val Met Arg Gln Gln Leu Thr Glu Leu Tyr Arg Asp Ile Phe Gln His
                325                 330                 335

Leu Arg Asp Glu Ser Gly Asn Ser Tyr Ser Pro Glu Glu Tyr Ala Leu
            340                 345                 350

Gln Gln Ala Ala Asp Gly Thr Ile Phe Leu Val Pro Arg Gly Thr Lys
            355                 360                 365

Met Glu Ala Thr Asp
    370
```

<210> SEQ ID NO 2
<211> LENGTH: 1676
<212> TYPE: DNA

<213> ORGANISM: Homo sapiens

<400> SEQUENCE: 2

```
gcatatactg tcatcatctt ggaaagaaaa ggctgagaac gtaaaactga ggacagagga      60
ggaaagcagg gtgacccctg atgttgccct agaaaatgga aaacaaaaca cagcaaaacg     120
aaaaacagaa gatctgactc tgcctttagc caggaaaaca gtttggggga gtaaaaagta    180
ttagggaaaa gagtgggcat tttgcctgga aaaaaggttt ctagagccat ctgggctttc    240
cgggaacctg gaccagactc tgcccagta ggatgtcccc gtgtcctccc cagcagagca    300
ggaacagggt gatacagctg tccacttcag agctaggaga gatggaactg acttggcagg    360
agatcatgtc catcaccgag ctgcagggtc tgaatgctcc aagtgagcca tcatttgagc    420
cccaagcccc agctccatac cttggacctc caccacccac aacttactgc ccctgctcaa    480
tccacccaga ttctggcttc ccacttcctc caccacctta tgagctccca gcatccacat    540
cccatgtccc agatccccca tactcctatg caacatggc cataccagtc tccaagccac    600
tgagcctctc aggcctgctc agtgagccgc tccaagaccc cttagccctc ctggacattg    660
ggctgccagc agggccacct aagccccaag aagacccaga atccgactca ggattatccc    720
tcaactatag cgatgctgaa tctcttgagc tggagggaca gaggctggt cggcggcgca    780
gcgaatatgt agagatgtac ccagtggagt acccctactc actcatgccc aactccttgg    840
cccactccaa ctataccttg ccagctgctg agaccccctt ggccttagag ccctcctcag    900
gccctgtgcg ggctaagccc actgcacggg gggaggcagg gagtcgggat gaacgtcggg    960
ccttggccat gaagattcct tttcctacgg acaagattgt caacttgccg gtagatgact   1020
ttaatgagct attggcaagg tacccgctga cagagagcca gctagcgcta gtccgggaca   1080
tccgacgacg gggcaaaaac aaggtggcag cccagaactg ccgcaagagg aagctggaaa   1140
ccattgtgca gctggagcgg agctggagc ggctgaccaa tgaacgggag cggcttctca   1200
gggcccgcgg ggaggcagac cggaccctgg aggtcatgcg ccaacagctg acagagctgt   1260
accgtgacat tttccagcac cttcgggatg aatcaggcaa cagctactct cctgaagagt   1320
acgcgctgca acaggctgcc gatgggacca tcttccttgt gccccggggg accaagatgg   1380
aggccacaga ctgagctggc ccagaggggt ggaactgctg atgggatttc cttcattccc   1440
ttctgataaa ggtactcccc aaccctgagt cccagaagga gctgagttct ctagaccaga   1500
agaggatgac aatggcaaca agtgtttgga agttccaagg tgtgttcaaa gaggcttgcc   1560
ttgagggagg gctggaatct gtcttccctg actcggctcc tcaggtcttt agcctccacc   1620
ttgtctaagc tttggtctat aaagtgcgct acagaaaaaa aaaaaaaaaa aaaaaa       1676
```

<210> SEQ ID NO 3
<211> LENGTH: 1654
<212> TYPE: DNA
<213> ORGANISM: Homo sapiens

<400> SEQUENCE: 3

```
gcatatactg tcatcatctt ggaaagaaaa ggctgagaac gtaaaactga ggacagagga      60
ggaaagcagg gtgacccctg atgttgccct agaaaatgga aaacaaaaca cagcaaaaca    120
gaaaaacaga gatctgact ctgcctttag ccaggaaaac agtttggggg agtaaaaagt    180
attagggaaa gagtgggca ttttgcctgg aaaaaaggtt tctagagcca tctgggcttt    240
ccgggaacct ggaccagact ctgcccagt aggatgtccc cgtgtcctcc ccagcagagc    300
aggaacaggg tgatacagct gtccacttca gagctaggag agatggaact gacttggcag    360
```

```
gagatcatgt ccatcaccga gctgcagggt ctgaatgctc caagtgagcc atcatttgag    420
cccccaagccc cagctccata ccttggacct ccaccaccca caacttactg ccccctgctca   480
atccacccag attctggctt cccacttcct ccaccacctt atgagctccc agcatccaca   540
tcccatgtcc cagatccccc atactcctat ggcaacatgg ccataccagt ctccaagcca   600
ctgagcctct caggcctgct cagtgagccg ctccaagacc ccttagccct cctggacatt   660
gggctgccag cagggccacc taagcccaa gaagacccag aatccgactc aggattatcc    720
ctcaactata gcgatgctga atctcttgag ctggaggga cagaggctgg tcggcggcgc    780
agcgaatatg tagagatgta cccagtggag taccccctact cactcatgcc caactccttg   840
gcccactcca actatacctt gccagctgct gagacccct tggccttaga gccctcctca    900
ggccctgtgc gggctaagcc cactgcacgg ggggaggcag ggagtcggga tgaacgtcgg   960
gccttggcca tgaagattcc ttttcctacg acaagattg tcaacttgcc ggtagatgac   1020
tttaatgagc tattggcaag gtacccgctg acagccagct agcgctagtc cgggacatcc   1080
gacgacgggg caaaaacaag gtggcagccc agaactgccg caagaggaag ctggaaacca   1140
ttgtgcagct ggagcgggag ctggagcggc tgaccaatga acgggagcgg cttctcaggg   1200
cccgcgggga ggcagaccgg accctggagg tcatgcgcca acagctgaca gagctgtacc   1260
gtgacatttt ccagcacctt cgggatgaat caggcaacag ctactctcct gaagagtacg   1320
cgctgcaaca ggctgccgat gggaccatct tccttgtgcc ccgggggacc aagatggagg   1380
ccacagactg agctggccca gaggggtgga actgctgatg ggatttcctt cattcccttc   1440
tgataaaggt actccccaac cctgagtccc agaaggagct gagttctcta gaccagaaga   1500
ggatgacaat gcaacaagt gtttggaagt tccaaggtgt gttcaaagag gcttgccttg   1560
agggagggct ggaatctgtc ttccctgact cggctcctca ggtctttagc ctccaccttg   1620
tctaagcttt ggtctataaa gtgcgctaca gaaa                                1654
```

<210> SEQ ID NO 4
<211> LENGTH: 262
<212> TYPE: PRT
<213> ORGANISM: Homo sapiens

<400> SEQUENCE: 4

Met Ser Pro Cys Pro Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
    50                  55                  60

Tyr Cys Pro Cys Ser Ile His Pro Asp Ser Gly Phe Pro Leu Pro Pro
65                  70                  75                  80

Pro Pro Tyr Glu Leu Pro Ala Ser Thr Ser His Val Pro Asp Pro Pro
                85                  90                  95

Tyr Ser Tyr Gly Asn Met Ala Ile Pro Val Ser Lys Pro Leu Ser Leu
            100                 105                 110

Ser Gly Leu Leu Ser Glu Pro Leu Gln Asp Pro Leu Ala Leu Leu Asp
        115                 120                 125

Ile Gly Leu Pro Ala Gly Pro Pro Lys Pro Gln Glu Asp Pro Glu Ser
    130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Arg Ser Glu Tyr Val Glu Met Tyr
                165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
        195                 200                 205

Ser Gly Pro Val Arg Ala Lys Pro Thr Ala Arg Gly Glu Ala Gly Ser
    210                 215                 220

Arg Asp Glu Arg Arg Ala Leu Ala Met Lys Ile Pro Phe Pro Thr Asp
225                 230                 235                 240

Lys Ile Val Asn Leu Pro Val Asp Asp Phe Asn Glu Leu Leu Ala Arg
                245                 250                 255

Tyr Pro Leu Thr Ala Ser
            260

<210> SEQ ID NO 5
<211> LENGTH: 1659
<212> TYPE: DNA
<213> ORGANISM: Homo sapiens

<400> SEQUENCE: 5
gcatatactg tcatcatctt ggaaagaaaa ggctgagaac gtaaaactga ggacagagga      60
ggaaagcagg gtgacccctg atgttgccct agaaatgga aaacaaaaca cagcaaaaca     120
gaaaaacaga gatctgact ctgcctttag ccaggaaaac agtttggggg agtaaaaagt     180
attagggaaa agagtgggca ttttgcctgg aaaaaaggtt tctagagcca tctgggcttt     240
ccgggaacct ggaccagact ctgcccagt aggatgtccc cgtgtcctcc ccagcagagc     300
aggaacaggg tgatacagct gtccacttca gagctaggag agatggaact gacttggcag     360
gagatcatgt ccatcaccga gctgcagggt ctgaatgctc caagtgagcc atcatttgag     420
ccccaagccc cagctccata ccttggacct ccaccaccca caacttactg ccctgctca     480 atccacccag attctggctt cccacttcct ccaccaccctt atgagctccc agcatccaca     540
tcccatgtcc cagatccccc atactcctat ggcaacatgg ccataccagt ctccaagcca     600
ctgagcctct caggcctgct cagtgagccg ctccaagacc ccttagccct cctggacatt     660
gggctgccag cagggccacc taagccccaa gagacccag aatccgactc aggattatcc     720
ctcaactata gcgatgctga atctcttgag ctggagggga cagaggctgg tcggcggcgc     780
agcgaatatg tagagatgta cccagtggag taccctact cactcatgcc caactccttg     840
gcccactcca actataccctt gccagctgct gagaccccct tggccttaga gccctcctca     900
ggccctgtgc gggctaagcc cactgcacgg ggggaggcag ggagtcggga tgaacgtcgg     960
gccttggcca tgaagattcc ttttcctacg gacaagattg tcaacgttgc cggtagatga    1020
ctttaatgag ctattggcaa ggtacccgct gacagagagc cagctagcgc tagtccggga    1080
catccgacga cggggcaaaa acaaggtggc agcccagaac tgccgcaaga ggaagctgga    1140
aaccattgtg cagctggagc gggagctgga gcggctgacc aatgaacggg agcggcttct    1200
cagggcccgc ggggaggcag accggaccct ggaggtcatg cgccaacagc tgacagagct    1260
gtaccgtgac atttttccagc accttcggga tgaatcaggc aacagctact ctcctgaaga    1320
gtacgcgctg caacaggctg ccgatgggac catcttcctt gtgccccggg ggaccaagat    1380

```
ggaggccaca gactgagctg cccagaggg gtggaactgc tgatgggatt tccttcattc    1440
ccttctgata aggtactcc ccaaccctga gtcccagaag gagctgagtt ctctagacca    1500
gaagaggatg acaatggcaa caagtgtttg gaagttccaa ggtgtgttca agaggcttg    1560 ccttgaggga gggctggaat ctgtcttccc tgactcggct cctcaggtct ttagcctcca    1620
ccttgtctaa gctttggtct ataaagtgcg ctacagaaa                          1659
```

<210> SEQ ID NO 6
<211> LENGTH: 248
<212> TYPE: PRT
<213> ORGANISM: Homo sapiens

<400> SEQUENCE: 6

```
Met Ser Pro Cys Pro Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
50                  55                  60

Tyr Cys Pro Cys Ser Ile His Pro Asp Ser Gly Phe Pro Leu Pro Pro
65                  70                  75                  80

Pro Pro Tyr Glu Leu Pro Ala Ser Thr Ser His Val Pro Asp Pro Pro
                85                  90                  95

Tyr Ser Tyr Gly Asn Met Ala Ile Pro Val Ser Lys Pro Leu Ser Leu
            100                 105                 110

Ser Gly Leu Leu Ser Glu Pro Leu Gln Asp Pro Leu Ala Leu Leu Asp
        115                 120                 125

Ile Gly Leu Pro Ala Gly Pro Pro Lys Pro Gln Glu Asp Pro Glu Ser
130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Ser Glu Tyr Val Glu Met Tyr
            165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
        195                 200                 205

Ser Gly Pro Val Arg Ala Lys Pro Thr Ala Arg Gly Glu Ala Gly Ser
    210                 215                 220

Arg Asp Glu Arg Arg Ala Leu Ala Met Lys Ile Pro Phe Pro Thr Asp
225                 230                 235                 240

Lys Ile Val Asn Val Ala Gly Arg
                245
```

<210> SEQ ID NO 7
<211> LENGTH: 1659
<212> TYPE: DNA
<213> ORGANISM: Homo sapiens

<400> SEQUENCE: 7

```
gcatatactg tcatcatctt ggaaagaaaa ggctgagaac gtaaaactga ggacagagga    60
ggaaagcagg gtgaccctg atgttgccct agaaatgga aaacaaaaca cagcaaaaca   120
gaaaaacaga agatctgact ctgcctttag ccaggaaaac agtttggggg agtaaaaagt   180
```

```
attagggaaa agagtgggca ttttgcctgg aaaaaaggtt tctagagcca tctgggcttt      240
ccgggaacct ggaccagact ctggcccagt aggatgtccc cgtgtcctcc ccagcagagc      300
aggaacaggg tgatacagct gtccacttca gagctaggag agatggaact gacttggcag      360
gagatcatgt ccatcaccga gctgcagggt ctgaatgctc aagtgagcc atcatttgag       420 ccccaagccc cagctccata ccttggacct ccaccaccca aacttactg cccctgctca       480 atccacccag attctggctt cccacttcct ccaccacctt atgagctccc agcatccaca      540
tcccatgtcc cagatccccc atactcctat ggcaacatgg ccataccagt ctccaagcca      600
ctgagcctct caggcctgct cagtgagccg ctccaagacc cttagccct cctggacatt       660 gggctgccag cagggccacc taagccccaa gagacccag aatccgactc aggattatcc       720
ctcaactata gcgatgctga atctcttgag ctggaggga cagaggctgg tcggcggcgc       780
agcgaatatg tagagatgta cccagtggag taccccctact cactcatgcc caactccttg      840
gcccactcca actataccct tgccagctgct gagacccct tggccttaga gccctcctca      900
ggccctgtgc gggctaagcc cactgcacgg gggggaggca gggagtcggg atgaacgtcg      960
ggccttggcc atgaagattc ctttcctac ggacaagatt gtcaacttgc cggtagatga      1020
ctttaatgag ctattggcaa ggtacccgct gacagagagc cagctagcgc tagtccggga    1080
catccgacga cggggcaaaa acaaggtggc agcccgaac tgccgcaaga ggaagctgga     1140
aaccattgtg cagctggagc gggagctgga gcggctgacc aatgaacggg agcggcttct   1200
cagggcccgc ggggaggcag accggaccct ggaggtcatg cgccaacagc tgacagagct   1260
gtaccgtgac attttccagc accttcggga tgaatcaggc aacagctact ctcctgaaga   1320
gtacgcgctg caacaggctg ccgatgggac catcttcctt gtgccccggg ggaccaagat   1380
ggaggccaca gactgagctg gcccagaggg gtggaactgc tgatgggatt ccttcattc    1440 ccttctgata aggtactcc ccaaccctga gtcccagaag gagctgagtt ctctagacca     1500
gaagaggatg acaatggcaa caagtgtttg gaagttccaa ggtgtgttca aagaggcttg   1560
ccttgaggga gggctggaat ctgtcttccc tgactcggct cctcaggtct ttagcctcca   1620
ccttgtctaa gctttggtct ataaagtgcg ctacagaaa                           1659

<210> SEQ ID NO 8
<211> LENGTH: 226
<212> TYPE: PRT
<213> ORGANISM: Homo sapiens

<400> SEQUENCE: 8

Met Ser Pro Cys Pro Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
    50                  55                  60

Tyr Cys Pro Cys Ser Ile His Pro Asp Ser Gly Phe Pro Leu Pro
65                  70                  75                  80

Pro Pro Tyr Glu Leu Pro Ala Ser Thr Ser His Val Pro Asp Pro
                85                  90                  95

Tyr Ser Tyr Gly Asn Met Ala Ile Pro Val Ser Lys Pro Leu Ser Leu
            100                 105                 110
```

```
Ser Gly Leu Leu Ser Glu Pro Leu Gln Asp Pro Leu Ala Leu Leu Asp
        115                 120                 125

Ile Gly Leu Pro Ala Gly Pro Pro Lys Pro Gln Glu Asp Pro Glu Ser
    130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Ser Glu Tyr Val Met Tyr
                165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
        195                 200                 205

Ser Gly Pro Val Arg Ala Lys Pro Thr Ala Arg Gly Gly Gly Arg Glu
    210                 215                 220

Ser Gly
225

<210> SEQ ID NO 9
<211> LENGTH: 1646
<212> TYPE: DNA
<213> ORGANISM: Homo sapiens

<400> SEQUENCE: 9
gcatatactg tcatcatctt ggaaagaaaa ggctgagaac gtaaaactga ggacagagga      60
ggaaagcagg gtgaccoctg atgttgccct agaaatgga aaacaaaaca cagcaaaaca     120
gaaaaacaga agatctgact ctgcctttag ccaggaaaac agtttggggg agtaaaaagt     180
attagggaaa agagtgggca ttttgcctgg aaaaaaggtt tctagagcca tctgggcttt     240
ccgggaacct ggaccagact ctgcccagt aggatgtccc cgtgtcctcc ccagcagagc      300
aggaacaggg tgatacagct gtccacttca gagctaggag agatggaact gacttggcag     360
gagatcatgt ccatcaccga gctgcagggt ctgaatgctc caagtgagcc atcatttgag     420
ccccaagccc cagctccata ccttggacct ccaccaccca aacttactg ccctgctca      480 atccacccag attctggctt cccacttcct ccaccacctt atgagctccc agcatccaca     540
tcccatgtcc cagatccccc atactcctat ggcaacatgg ccataccagt ctccaagcca     600
ctgagcctct caggcctgct cagtgagccg ctccaagacc ccttagccct cctggacatt     660
gggctgccag cagggccacc taagccccaa gaagacccag aatccgactc aggattatcc     720
ctcaactata gcgatgctga atctcttgag ctggagggga cagaggctgg tcggcggcgc     780
agcgaatatg tagagatgta cccagtggag tacccctact cactcatgcc caactccttg     840
gcccactcca actataacct tgccagctgct gagacccct tggccttaga gccctcctca     900
ggccctgtgc gggctaagcc cactgcacgg ggggaggcag ggagtcggga tgaacgtcgg     960
gccttggcca tgaagattcc ttttcctacg acaagattg tcaacttgcc ggtagatgac    1020
tttaatgagc tattggcaag gtacccgctg acagagagcc agctagcgct agtccgggac    1080
atccgacgac ggggcaaaaa caaggtggca gcccagaact gccgcaagag gaagctggaa    1140
accattgtgc agctggagcg gctgaccaat aacgggagc ggcttctcag ggcccgcggg    1200
gaggcagacc ggaccctgga ggtcatgcgc caacagctga cagagctgta ccgtgacatt    1260
ttccagcacc ttcgggatga atcaggcaac agctactctc ctgaagagta cgcgctgcaa    1320
caggctgccg atgggaccat cttccttgtg ccccggggga ccaagatgga ggccacagac    1380
```

-continued

```
tgagctggcc cagaggggtg gaactgctga tgggatttcc ttcattccct tctgataaag    1440
gtactcccca accctgagtc ccagaaggag ctgagttctc tagaccagaa gaggatgaca    1500
atggcaacaa gtgtttggaa gttccaaggt gtgttcaaag aggcttgcct tgagggaggg    1560
ctggaatctg tcttccctga ctcggctcct caggtcttta gcctccacct tgtctaagct    1620
ttggtctata aagtgcgcta cagaaa                                          1646
```

<210> SEQ ID NO 10
<211> LENGTH: 369
<212> TYPE: PRT
<213> ORGANISM: Homo sapiens

<400> SEQUENCE: 10

```
Met Ser Pro Cys Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
    50                  55                  60

Tyr Cys Pro Cys Ser Ile His Pro Asp Ser Gly Phe Pro Leu Pro Pro
65                  70                  75                  80

Pro Pro Tyr Glu Leu Pro Ala Ser Thr His Val Pro Asp Pro Pro
                85                  90                  95

Tyr Ser Tyr Gly Asn Met Ala Ile Pro Val Ser Lys Pro Leu Ser Leu
            100                 105                 110

Ser Gly Leu Leu Ser Glu Pro Leu Gln Asp Pro Leu Ala Leu Leu Asp
        115                 120                 125

Ile Gly Leu Pro Ala Gly Pro Pro Lys Pro Gln Glu Asp Pro Glu Ser
    130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Arg Ser Glu Tyr Val Glu Met Tyr
                165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
        195                 200                 205

Ser Gly Pro Val Arg Ala Lys Pro Thr Ala Arg Gly Glu Ala Gly Ser
    210                 215                 220

Arg Asp Glu Arg Arg Ala Leu Ala Met Lys Ile Pro Phe Pro Thr Asp
225                 230                 235                 240

Lys Ile Val Asn Leu Pro Val Asp Asp Phe Asn Glu Leu Leu Ala Arg
                245                 250                 255

Tyr Pro Leu Thr Glu Ser Gln Leu Ala Leu Val Arg Asp Ile Arg Arg
            260                 265                 270

Arg Gly Lys Asn Lys Val Ala Ala Gln Asn Cys Arg Lys Arg Lys Leu
        275                 280                 285

Glu Thr Ile Val Gln Leu Glu Arg Leu Thr Asn Glu Arg Glu Arg Leu
    290                 295                 300

Leu Arg Ala Arg Gly Glu Ala Asp Arg Thr Leu Glu Val Met Arg Gln
305                 310                 315                 320

Gln Leu Thr Glu Leu Tyr Arg Asp Ile Phe Gln His Leu Arg Asp Glu
```

```
                      325                 330                 335
        Ser Gly Asn Ser Tyr Ser Pro Glu Glu Tyr Ala Leu Gln Gln Ala Ala
                340                 345                 350

Asp Gly Thr Ile Phe Leu Val Pro Arg Gly Thr Lys Met Glu Ala Thr
                    355                 360                 365

Asp

<210> SEQ ID NO 11
<211> LENGTH: 1657
<212> TYPE: DNA
<213> ORGANISM: Homo sapiens

<400> SEQUENCE: 11
gcatatactg tcatcatctt ggaaagaaaa ggctgagaac gtaaaactga ggacagagga      60
ggaaagcagg gtgacccctg atgttgccct agaaaatgga aaacaaaaca cagcaaaaca    120
gaaaaacaga gatctgact ctgcctttag ccaggaaaac agtttggggg agtaaaaagt     180
attagggaaa agagtgggca ttttgcctgg aaaaaaggtt tctagagcca tctgggcttt    240
ccgggaacct ggaccagact ctggcccagt aggatgtccc cgtgtcctcc ccagcagagc    300
aggaacaggg tgatacagct gtccacttca gagctaggag agatggaact gacttggcag    360
gagatcatgt ccatcaccga gctgcagggt ctgaatgctc aagtgagcc atcatttgag     420 ccccaagccc cagctccata ccttggacct ccaccaccca aacttactg ccctgctca      480 atccacccag attctggctt cccacttctc caccacctta tgagctccca gcatccacat    540
cccatgtccc agatccccca tactcctatg caacatggc cataccagtc tccaagccac     600
tgagcctctc aggcctgctc agtgagccgc tccaagaccc cttagccctc ctggacattg    660
ggctgccagc agggccacct aagccccaag aagacccaga atccgactca ggattatccc    720
tcaactatag cgatgctgaa tctcttgagc tgagggga cagaggctggt cggcggcgca     780 gcgaatatgt agagatgtac ccagtggagt acccctactc actcatgccc aactccttgg    840
cccactccaa ctataccttg ccagctgctg agaccccctt ggccttagag ccctcctcag    900
gccctgtgcg ggctaagccc actgcacggg ggaggcagg gagtcgggat gaacgtcggg    960
ccttggccat gaagattcct tttcctacgg acaagattgt caacttgccg gtagatgact   1020
ttaatgagct attggcaagg tacccgctga cagagagcca gctagcgcta gtccgggaca   1080
tccgacgacg gggcaaaaac aaggtggcag cccagaactg ccgcaagagg aagctggaaa   1140
ccattgtgca gctggagcgg agctggagc ggctgaccaa tgaacgggag cggcttctca    1200
gggcccgcgg ggaggcagac cggacccctgg aggtcatgcg ccaacagctg acagagctgt   1260
accgtgacat tttccagcac cttcgggatg aatcaggcaa cagctactct cctgaagagt   1320
acgcgctgca acaggctgcc gatgggacca tcttccttgt gccccggggg accaagatgg   1380
aggccacaga ctgagctggc ccagaggggt ggaactgctg atgggatttc cttcattccc   1440
ttctgataaa ggtactcccc aaccctgagt cccagaagga gctgagttct ctagaccaga   1500
agaggatgac aatggcaaca agtgtttgga agttccaagg tgtgttcaaa gaggcttgcc   1560
ttgagggagg gctggaatct gtcttccctg actcggctcc tcaggtcttt agcctccacc   1620
ttgtctaagc tttggtctat aaagtgcgct acagaaa                            1657

<210> SEQ ID NO 12
<211> LENGTH: 109
<212> TYPE: PRT
<213> ORGANISM: Homo sapiens
```

<400> SEQUENCE: 12

```
Met Ser Pro Cys Pro Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
    50                  55                  60

Tyr Cys Pro Cys Ser Ile His Pro Asp Ser Gly Phe Pro Leu Leu His
65                  70                  75                  80

His Leu Met Ser Ser Gln His Pro His Pro Met Ser Gln Ile Pro His
                85                  90                  95

Thr Pro Met Ala Thr Trp Pro Tyr Gln Ser Pro Ser His
            100                 105
```

<210> SEQ ID NO 13
<211> LENGTH: 1659
<212> TYPE: DNA
<213> ORGANISM: Homo sapiens

<400> SEQUENCE: 13

| | |
|---|---:|
| gcatatactg tcatcatctt ggaaagaaaa ggctgagaac gtaaaactga ggacagagga | 60 |
| ggaaagcagg gtgacccctg atgttgccct agaaatggaa aacaaaaca cagcaaaaca | 120 |
| gaaaaacaga gatctgact ctgcctttag ccaggaaaac agtttggggg agtaaaaagt | 180 |
| attagggaaa agagtgggca ttttgcctgg aaaaaggtt tctagagcca tctgggcttt | 240 |
| ccgggaacct ggaccagact ctggcccagt aggatgtccc cgtgtcctcc ccagcagagc | 300 |
| aggaacaggg tgatacagct gtccacttca gagctaggag agatggaact gacttggcag | 360 |
| gagatcatgt ccatcaccga gctgcagggt ctgaatgctc caagtgagcc atcatttgag | 420 |
| ccccaagccc cagctccata ccttggacct ccaccaccca caacttactg ccctgctca | 480 |
| atccacccag attctggctt cccacttcct ccaccacctt atgagctccc agcatccaca | 540 |
| tcccatgtcc cagatccccc atactcctat ggcaacatgg ccataccagt ctccaagcca | 600 |
| ctgagcctct caggcctgct cagtgagccg ctccaagacc ccttagccct cctggacatt | 660 |
| gggctgccag cagggccacc taagccccaa gaagacccag aatccgactc aggattatcc | 720 |
| ctcaactata gcgatgctga atctcttgag ctggagggga cagaggctgg tcggcggcgc | 780 |
| agcgaatatg tagagatgta cccagtggag taccccctact cactcatgcc caactccttg | 840 |
| gcccactcca actataccct tgccagctgct gagacccctt ggccttaga gccctcctca | 900 |
| ggccctgtgc gggctaagcc cactgcacgg ggggaggcag ggagtcggga tgaacgtcgg | 960 |
| gccttggcca tgaagattcc ttttcctacg acaagattg tcaacttgcc ggtagatgac | 1020 |
| tttaatgagc tattggcaag gtaccccgctg acaagagagc cagctagcgc tagtccggga | 1080 |
| catccgacga cggggcaaaa acaaggtggc agcccagaac tgccgcaaga ggaagctgga | 1140 |
| aaccattgtg cagctggagc gggagctgga gcggctgacc aatgaacggg agcggcttct | 1200 |
| cagggcccgc ggggaggcag accggaccct ggaggtcatg cgccaacagc tgacagagct | 1260 |
| gtaccgtgac attttccagc accttcggga tgaatcaggc aacagctact ctcctgaaga | 1320 |
| gtacgcgctc aacaggctg ccgatgggac catcttcctt gtgccccggg ggaccaagat | 1380 |
| ggaggccaca gactgagctg gcccagaggg gtggaactgc tgatgggatt tccttcattc | 1440 |

```
ccttctgata aaggtactcc ccaaccctga gtcccagaag gagctgagtt ctctagacca    1500
gaagaggatg acaatggcaa caagtgtttg gaagttccaa ggtgtgttca aagaggcttg    1560
ccttgaggga gggctggaat ctgtcttccc tgactcggct cctcaggtct ttagcctcca    1620
ccttgtctaa gctttggtct ataaagtgcg ctacagaaa                          1659
```

<210> SEQ ID NO 14
<211> LENGTH: 303
<212> TYPE: PRT
<213> ORGANISM: Homo sapiens

<400> SEQUENCE: 14

```
Met Ser Pro Cys Pro Gln Gln Ser Arg Asn Arg Val Ile Gln Leu
1               5                   10                  15

Ser Thr Ser Glu Leu Gly Glu Met Glu Leu Thr Trp Gln Glu Ile Met
            20                  25                  30

Ser Ile Thr Glu Leu Gln Gly Leu Asn Ala Pro Ser Glu Pro Ser Phe
        35                  40                  45

Glu Pro Gln Ala Pro Ala Pro Tyr Leu Gly Pro Pro Pro Thr Thr
    50                  55                  60

Tyr Cys Pro Cys Ser Ile His Pro Asp Ser Gly Phe Pro Leu Pro Pro
65                  70                  75                  80

Pro Pro Tyr Glu Leu Pro Ala Ser Thr Ser His Val Pro Asp Pro Pro
                85                  90                  95

Tyr Ser Tyr Gly Asn Met Ala Ile Pro Val Ser Lys Pro Leu Ser Leu
            100                 105                 110

Ser Gly Leu Leu Ser Glu Pro Leu Gln Asp Pro Leu Ala Leu Leu Asp
        115                 120                 125

Ile Gly Leu Pro Ala Gly Pro Pro Lys Pro Gln Glu Asp Pro Glu Ser
    130                 135                 140

Asp Ser Gly Leu Ser Leu Asn Tyr Ser Asp Ala Glu Ser Leu Glu Leu
145                 150                 155                 160

Glu Gly Thr Glu Ala Gly Arg Arg Ser Glu Tyr Val Glu Met Tyr
                165                 170                 175

Pro Val Glu Tyr Pro Tyr Ser Leu Met Pro Asn Ser Leu Ala His Ser
            180                 185                 190

Asn Tyr Thr Leu Pro Ala Ala Glu Thr Pro Leu Ala Leu Glu Pro Ser
        195                 200                 205

Ser Gly Pro Val Arg Ala Lys Pro Thr Ala Arg Gly Glu Ala Gly Ser
    210                 215                 220

Arg Asp Glu Arg Arg Ala Leu Ala Met Lys Ile Pro Phe Pro Thr Asp
225                 230                 235                 240

Lys Ile Val Asn Leu Pro Val Asp Asp Phe Asn Glu Leu Leu Ala Arg
                245                 250                 255

Tyr Pro Leu Thr Arg Glu Pro Ala Ser Ala Ser Pro Gly His Pro Thr
            260                 265                 270

Thr Gly Gln Lys Gln Gly Gly Ser Pro Glu Leu Pro Gln Glu Glu Ala
        275                 280                 285

Gly Asn His Cys Ala Ala Gly Ala Gly Ala Gly Ala Ala Asp Gln
    290                 295                 300
```

<210> SEQ ID NO 15
<211> LENGTH: 22
<212> TYPE: DNA
<213> ORGANISM: artificial sequence

```
<220> FEATURE:
<223> OTHER INFORMATION: primer

<400> SEQUENCE: 15
tctttctggc ctggaggcta tc                                              22

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
tgctggatga cgtgagtaaa cc                                              22

<210> SEQ ID NO 17
<211> LENGTH: 16
<212> TYPE: DNA
<213> ORGANISM: artificial sequence
<220> FEATURE:
<223> OTHER INFORMATION: probe

<400> SEQUENCE: 17
agcgtactcc aaagat                                                     16

<210> SEQ ID NO 18
<211> LENGTH: 23
<212> TYPE: DNA
<213> ORGANISM: artificial sequence
<220> FEATURE:
<223> OTHER INFORMATION: primer

<400> SEQUENCE: 18
cggtctctcc ttccctcagg gga                                             23

<210> SEQ ID NO 19
<211> LENGTH: 22
<212> TYPE: DNA
<213> ORGANISM: artificial sequence
<220> FEATURE:
<223> OTHER INFORMATION: primer

<400> SEQUENCE: 19
tcttctccga cacacggcct cc                                              22

<210> SEQ ID NO 20
<211> LENGTH: 26
<212> TYPE: DNA
<213> ORGANISM: artificial sequence
<220> FEATURE:
<223> OTHER INFORMATION: primer

<400> SEQUENCE: 20
tgcgactttc agaagaatcc agcttg                                          26

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
tggagtgggc caaggagttg gg                                              22
```

```
<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tcggcggcgc agcgaatatg                                                  20

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
gtagctgttg cctgattcat cccg                                             24

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
gaggtcatgc gccaacagct gac                                              23

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
tgctcagcct caagcccaaa tttt                                             24
```

METHOD FOR THE DIAGNOSIS OF MYELOID NEOPLASIAS AND SOLID TUMORS

PRIORITY

This application corresponds to the national phase of International Application No. PCT/EP2013/052361, filed Feb. 7, 2013, which, in turn, claims priority to European Patent Application No. 12.154405.0 filed Feb. 8, 2012, both of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Aug. 7, 2014, is named LNK_152_SequenceListing.txt and is 34,594 bytes in size.

FIELD OF THE INVENTION

The present invention relates to an ex vivo or in vitro method to determine the presence or absence of a mutation or a variation in the NF-E2 gene in a sample from a patient suffering from a myeloid neoplasm or solid tumor.

BACKGROUND OF THE INVENTION

The term "myeloid neoplasias" (MNs) encompasses several classes of disorders, among them myeloproliferative neoplasms (MPNs), myelodysplastic syndromes (MDS), acute myelogenous leukemia (AML), chronic myelogenous leukemia (CML), as well as related disorders.

Myeloproliferative neoplasms (MPNs), such as polycythemia vera (PV), essential thrombocythemia (ET) and myelofibrosis (MF) are clonal hematopoietic disorders typified by an overproduction of terminally differentiated cells in part as a result of hypersensitivity of marrow progenitor cells to hematopoietic growth factors.

The molecular etiology of myeloproliferative neoplasms (MPNs) remains incompletely understood, despite recent advances incurred through the discovery of a point mutation in the JAK2 kinase (JAK2$^{V617F}$) in a large proportion of patients. Several lines of evidence support the hypothesis that additional aberrations, either preceding or following acquisition of the JAK2$^{V617F}$ mutation, contribute to the pathophysiology of these disorders.

The transcription factor Nuclear factor erythroid-2 (NF-E2) is crucial for regulating erythroid-specific gene expression. Cloning of the NF-E2 p45 protein has revealed that it contains a basic region-leucine zipper (b-zip) domain which associates with proteins of the Maf family to form functional NF-E2 [Igarashi et al., Nature (1994), 367, 568-572].

Nuclear factor erythroid-2 (NF-E2), a hematopoietic transcription factor, is overexpressed in a large majority of patients with polycythemia vera (PV) (Goerttler et al. [British Journal of Hematology 129 (2005) 138-150]. NF-E2 is essential for platelet formation as knock-out mice die perinatally of hemorrhage due to thrombocytopenia. In addition, loss of NF-E2 also affects the erythroid lineage since surviving adult mice display mild anemia with compensatory reticulocytosis.

Wang et al. [Blood (2010), pp 254-266] have shown that the transcription factor NF-E2 is overexpressed not only in the majority of patients with polycythemia vera but also in patients with essential thrombocytemia (ET) and primary myelofibrosis (PMF) independent of the presence or absence of the JAK2 mutation.

Toki et al teach that the NF-E2 mRNA is transcribed from two alternative promotors called NF-E2 1A and NF-E2 1F which are located on different exons (exon 1A and exon 1F, respectively) Toki et al, 2000, Exp. Hematol. 28: 1113-1119). The exons 1A and 1F are non-coding. The translation of NF-E2 starts in exon 2 and is continued in exon 3.

SUMMARY OF THE INVENTION

The amino acid sequence of the wild-type transcription factor NF-E2 is shown in FIG. 1 and SEQ ID NO:1. The nucleic acid sequence coding for the wild-type NF-E2 transcription factor is shown in SEQ ID NO:2. The sequence of the complementary strand is not shown but can be deduced according to the general known rules of base pairing.

In the course of the present invention it has surprisingly been found that the degree of expression of the NF-E2 gene alone is not the only factor responsible for the promotion of erythroid maturation. It has been found that mutations occur within the transcription factor NF-E2 which have a strong influence on the maturation of progenitor cells leading ultimately to erythrocytes. The mutations as well as variants of NF-E2 gene could be detected in MPN patients and this fact can be utilized for diagnosis.

The physician frequently observes patients in the clinic suffering from a myeloid neoplasia whereby it is difficult to distinguish one disease from another. Such a differential diagnosis is, however, very often of utmost importance since depending on the diagnosis the physician selects the suitable therapy. It is therefore an object to provide an in vitro or ex vivo diagnostic method for distinguishing different types of myeloid neoplasias emcompassing myeloproliferative neoplasms, myelodysplastic syndromes, acute myelogenous leukemia, chronic myelogenous leukemia from reactive states, such as secondary erythrocytosis, secondary thrombocythemia and secondary leukocytosis. The diagnostic method can also be applied in patients suffering from a solid tumor.

It is therefore an object of the present invention to provide an ex vivo or in vitro method to determine the presence or absence of a mutation in the NF-E2 gene or of a variant in a sample from a patient suffering from a myeloid neoplasm or solid tumor whereby said method comprises:
a) obtaining a nucleic acid sample from the patient,
b) detecting the presence or absence of a variation or a mutation in the nucleic acid sample comprising the NF-E2 gene or a fragment thereof, whereby the presence of the variation or mutation is an indication of a myeloid neoplasm or a solid tumor.

BRIEF DESCRIPTION OF THE DRAWINGS

Important aspects of the present invention have been summarized in the Figures and can also be deduced from the sequence protocol.

FIG. 1 shows the sequence of the wild-type NF-E2 protein which is available under the accession number NP_006154. The nucleic acid sequence coding for the NF-E2 protein is shown in SEQ ID NO:2.

FIG. 2 shows the nucleic acid and the amino acid sequence derived therefrom of variant designated as F-209. At the N-terminus a mutation in exon 3 is shown. Due to a deletion a stop codon occurs and the protein ends with the amino acid sequence " . . . PLTAS".

The cDNA coding for the mutated protein of FIG. 2 is provided as SEQ ID NO:3 and the protein sequence of the sequence shown in FIG. 2 is provided in SEQ ID NO:4.

FIG. 3 shows another mutation in exon 3. The clone is designated as MPD-RC-241. In the nucleic acid sequence a "G" is inserted which results in a changed amino acid sequence at the N-terminus. The mutated sequence ends with the amino acids "-VNVAGR". The cDNA sequence is shown as SEQ ID NO:5 and the protein sequence of the mutated protein is shown as SEQ ID NO:6.

FIG. 4 shows another mutation in exon 3 (F-2836). The insertion of a "G" into the nucleic acid sequence results in the N-terminus of the mutated protein "-RGGGRESG". The cDNA sequence is shown as SEQ ID NO:7 and the protein sequence is shown as SEQ ID NO:8.

FIGS. 5A and 5B, which together make up FIG. 5, show another mutation in exon 3. The clone is designated as U-532. The cDNA is shown in SEQ ID NO:9 and the amino acid sequence is shown in SEQ ID NO:10.

FIG. 6 shows another mutation in exon 3 caused by a deletion of a "C". The amino acid sequence at the N-terminus is changed and the protein is shorter due to occurrence of a stop codon. The cDNA of clone U-409 is shown in SEQ ID NO:11 and the amino acid sequence is shown in SEQ ID NO:12.

FIGS. 7A and 7B, which together make up FIG. 7, show the sequence of a variant with the designation U-980. A mutation caused by an insertion of "A" results in a changed amino acid sequence at the N-terminus and the occurrence of a stop codon. The cDNA sequence is shown in SEQ ID NO:13. The amino acid sequence is provided as SEQ ID NO:14.

Figure 8:
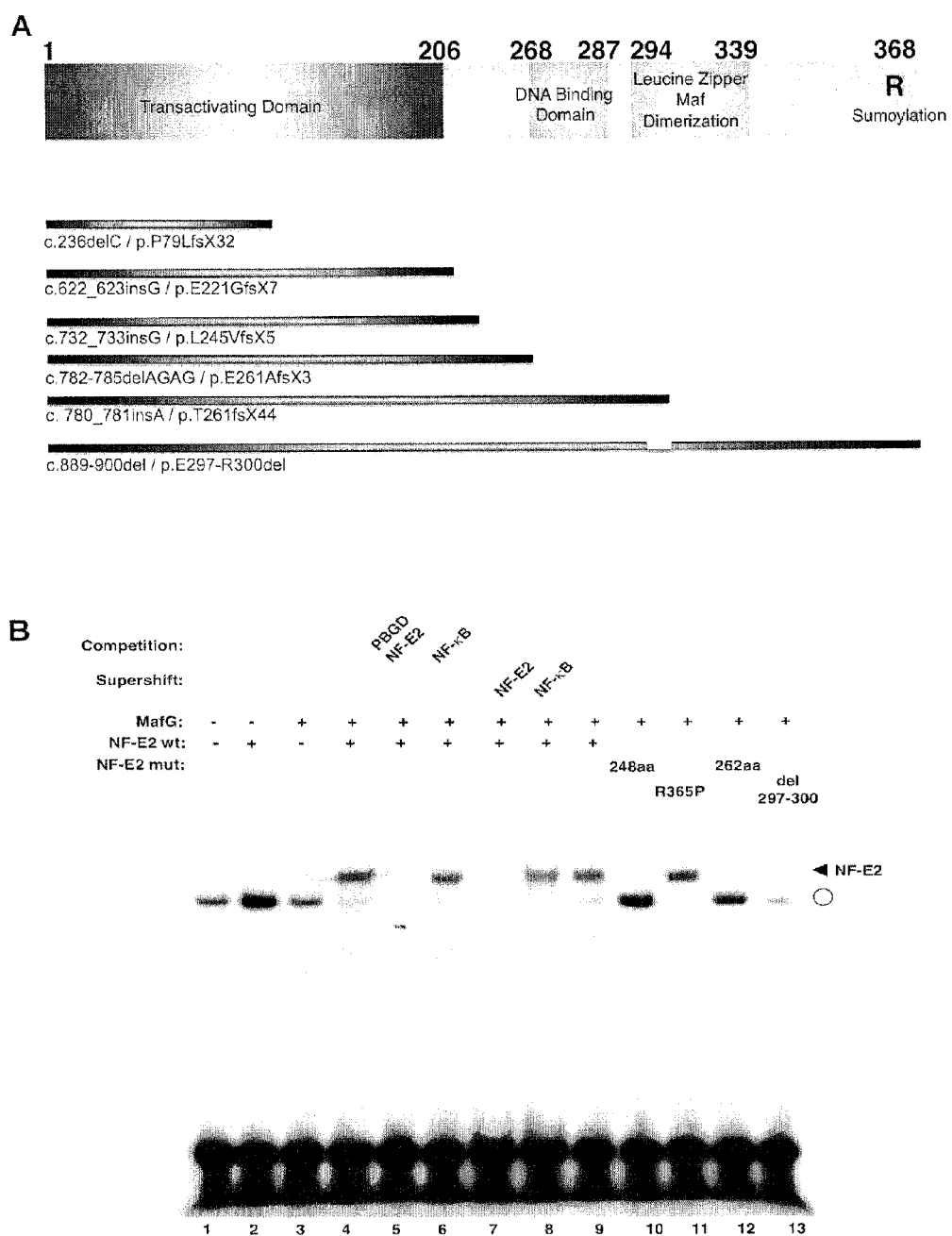
Figure 8:
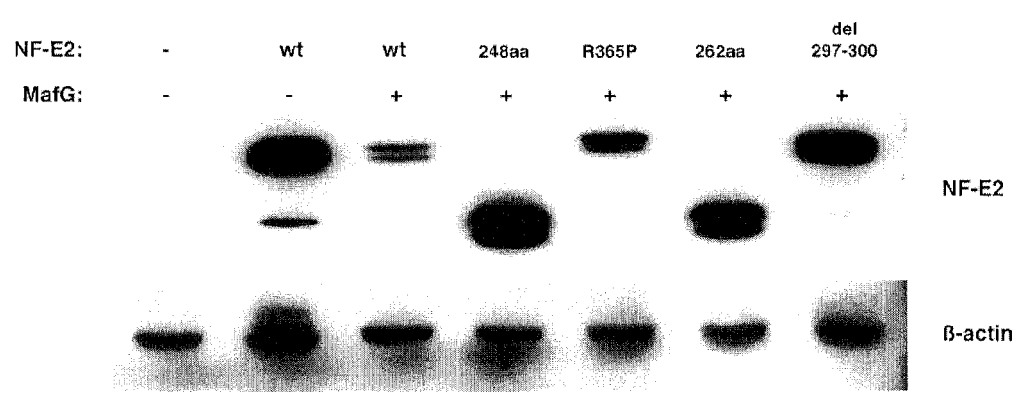

FIG. 8: NF-E2 mutations in MPN patients cause truncations and loss of DNA binding.

(A) Schematic representation of the NF-E2 protein (top) and the truncations resulting from mutations detected in MPN patients (bottom).

(B) Electrophoretic mobility shift assay (EMSA) of wt NF-E2 and NF-E2 mutants. Nuclear extracts of 293 cells transduced with expression vectors encoding either wt NF-E2 (lane 2), MafG (lane 3) or both (lanes 4-9) or the indicated NF-E2 mutants together with MafG (lanes 10-13) were incubated with a 32-P-labeled oligonucleotide containing a NF-E2 binding site (REF). In lanes 5 and 6, a 100× excess of a non-radioactive oligonucleotide, either consensus NF-E2 (lane 5) or a negative control, NF-κB (lane 7), was added. Alternatively, an antibody to NF-E2 (lane 7) or a control NF-κB antibody (lane 8) was added. A filled arrowhead indicates the specific NF-E2/DNA complex. The open circle shows nonspecific binding to the DNA probe.

(C) Protein expression in the cell extracts used for EMSA in (B). Cell lysates were subjected to SDS-PAGE and interrogated for NF-E2 (top) and beta-actin (bottom) expression by Western Blot.

Figure 9:
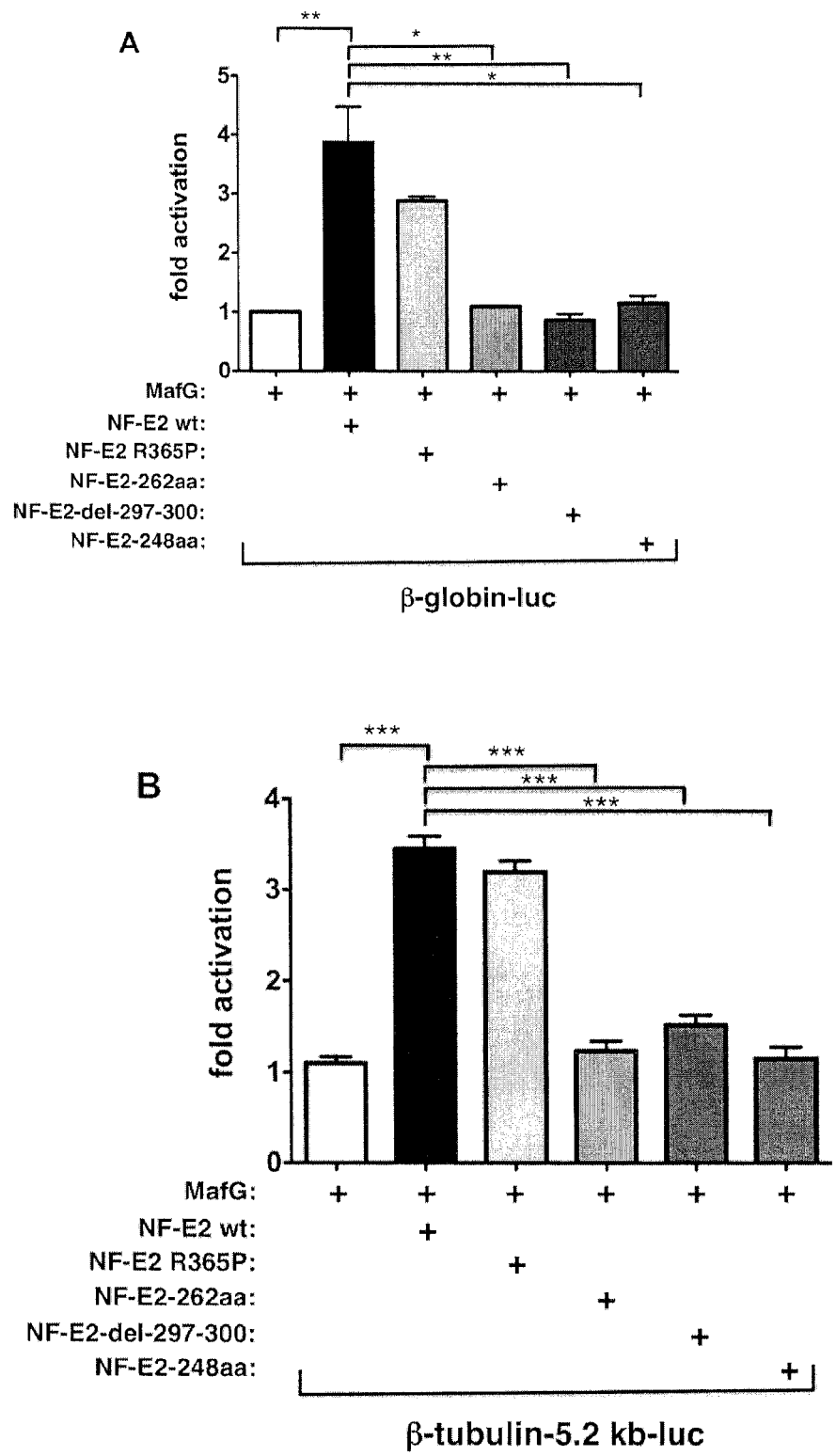
Figure 9:
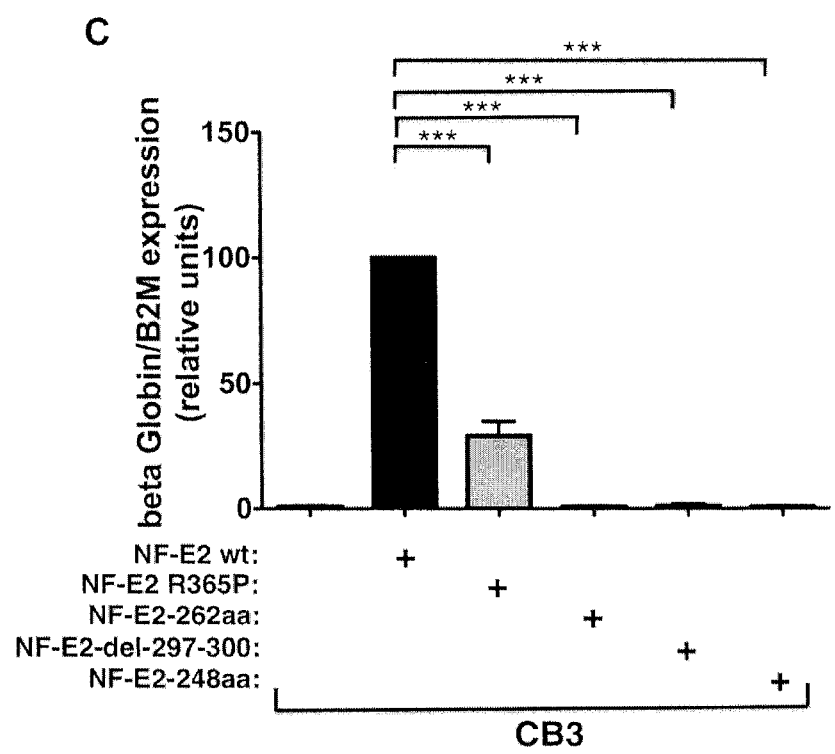
Figure 10:
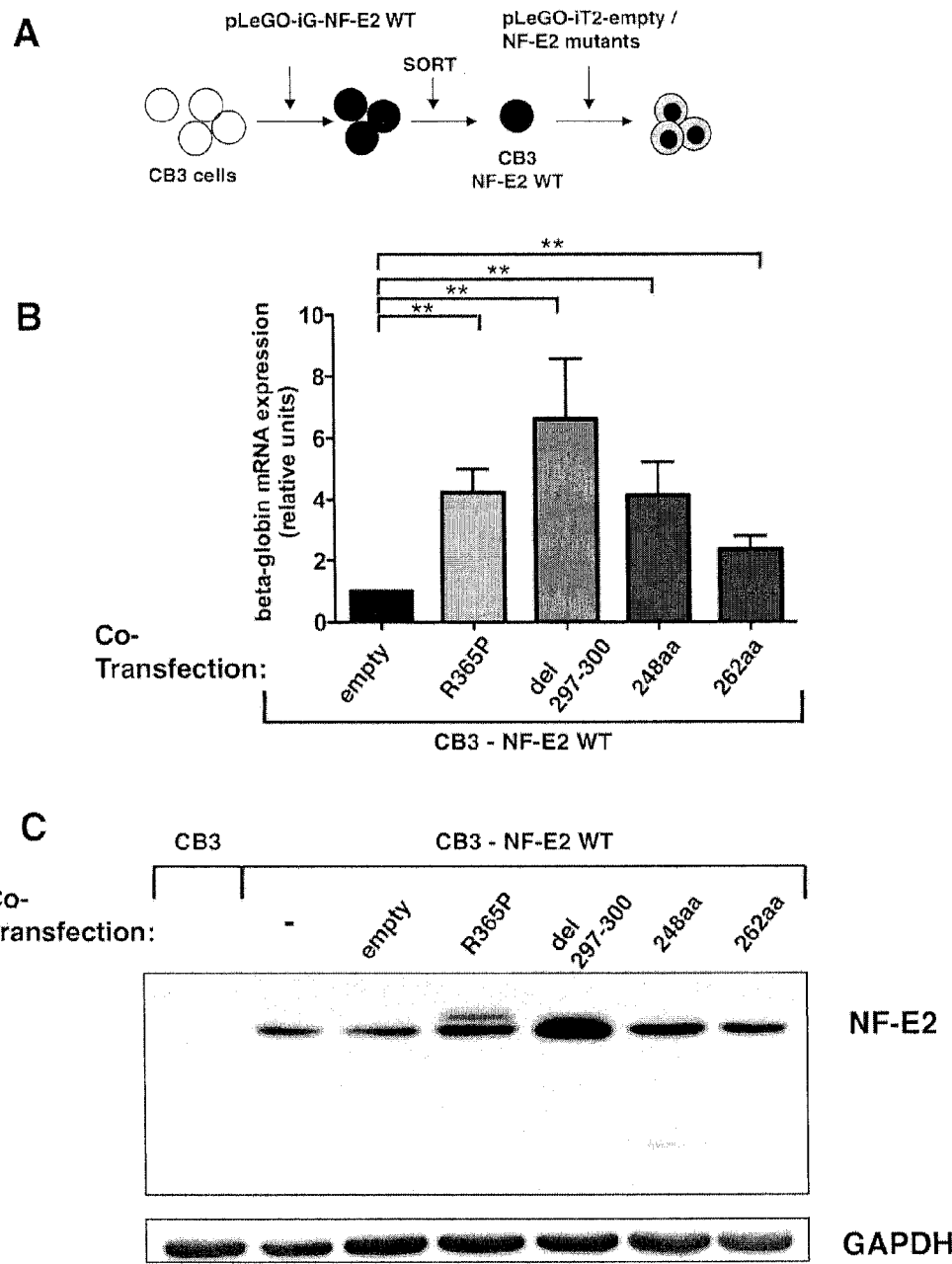

FIG. 9. Transactivating Activity of mutant NF-E2 proteins. Plasmids encoding (A) a beta-globin promoter-*luciferase* construct (Igarashi et al.) or (B) a reporter construct encoding 5.2 kb of the beta1-tubulin promoter coupled to the *luciferase* reporter gene were co-transfected into 293 cells either with expression vectors for MafG (white bars), wt NF-E2 (black bars) or various NF-E2 mutants (grey bars) as indicated. *Luciferase* activity was measured 16 hrs post-transfection and normalized for transfection efficiency by determination of *Renilla luciferase* activity from a co-transfected vector. Activity of MafG alone was set at 1 and fold activity relative to this control is depicted. Bar graphs represent the mean±SD of four independent experiments, each performed in duplicate,* $p<0.05$, $p<0.01$, * $p<0.001$ by One Way ANOVA with Bonferroni's post-hoc multiple comparison test. (C) CB3 cells, which lack endogenous NF-E2, were transfected with wt NF-E2 (black bars) or various NF-E2 mutants (grey bars) as indicated. 72 hours after transfection, RNA was harvested and assayed for beta-globin mRNA expression and beta-2-microglobulin housekeeping gene expression by qRT-PCR. Results are reported as relative expression levels setting beta-globin expression in untransfected CB3 cells at 1. Data were analyzed for statistical significance by One Way ANOVA with Bonferroni's post-hoc multiple comparison test. $p<0.01$; *$p<0.001$ FIG. 10. Effect of mutant NF-E2 proteins on NF-E2 wt activity. (A) Experimental design. CB3 cells were transduced with pLeGO-iG-NF-E2, sorted for GFP expression and a single clone (CB3-NF-E2 wt), which displays wt NF-E2 expression, selected. Subsequently, CB3-NF-E2 wt cells were transduced with either an empty pLeGo-iT vector, or with pLeGO-iT vectors encoding the indicated NF-E2 mutants. Double positive cells were FACS sorted and (B) assayed for beta-globin expression and beta-2-microglobulin housekeeping gene expression by qRT-PCR. Results are reported as relative expression levels setting beta-globin expression in empty pLeGO-iT transduced CB3-NF-E2 wt cells at 1. Data were analyzed for statistical significance by One Way ANOVA with Bonferroni's post-hoc multiple comparison test. ***$p<0.0001$. as well as NF-E2 and GAPDH protein expression (C) Protein expression in the transduced CB3 cells assayed for beta-globin expression in (B). Cell lysates were subjected to SDS-PAGE and interrogated for NF-E2 (top) and GAPDH (bottom) expression by Western Blot.

Figure 11:
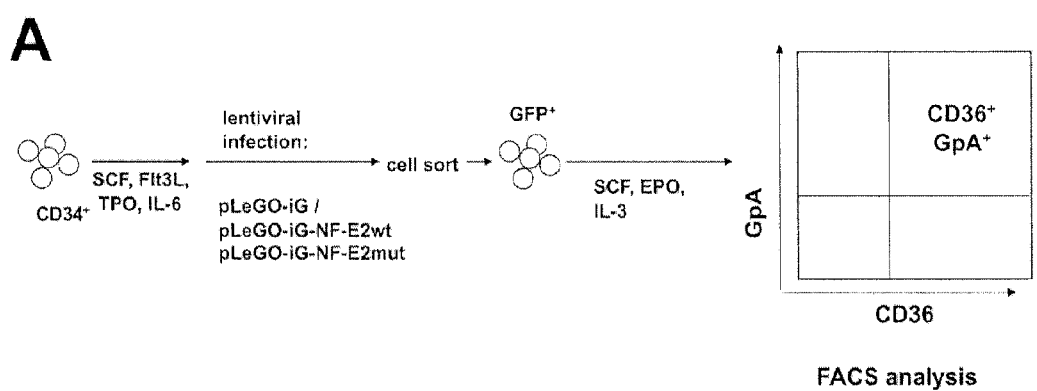
Figure 11:
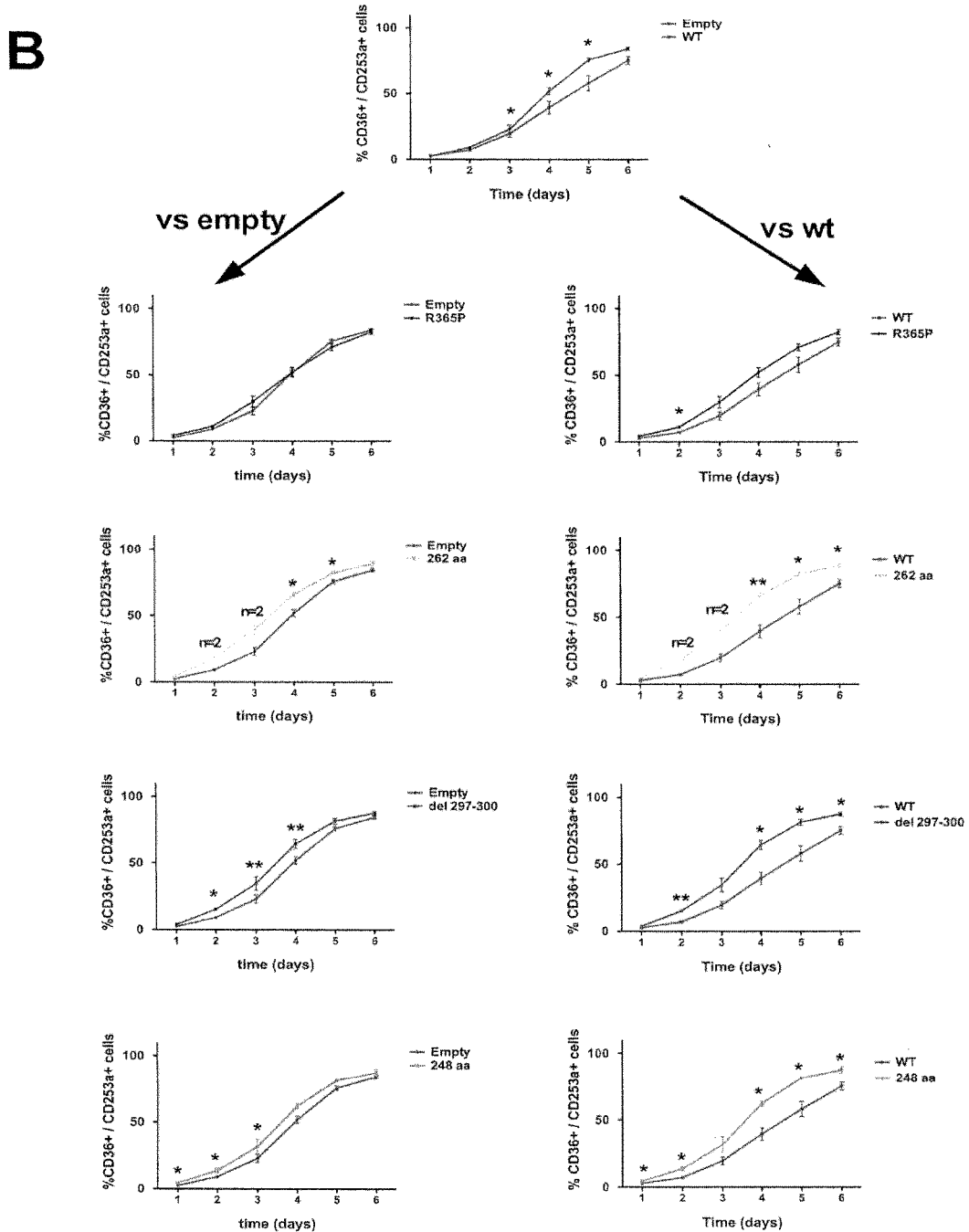

FIG. 11. Effect of NF-E2 mutations on erythroid maturation.

(A) Experimental design. CD34$^+$ cells were transduced with empty pLeGo-iG, with pLeGO-iG-NF-E2 wt or with pLeGO-iG carrying the indicated NF-E2 mutations. Cells were sorted for GFP expression to obtain pure populations of transduced cells and maintained in medium promoting erythroid differentiation. At the indicated time points, erythroid maturation was assessed by FACS analysis using CD36 and glycophrin A (GpA).

(B) Erythroid Maturation. The percentage of CD36$^+$/GpA$^+$ double positive erythroid cells is shown over time. Mean and standard error of n=4 independent experiments are depicted. (Left) Comparison of cells transduced with NF-E2 mutants to cells transduced with empty virus. (Right) comparison of cells transduced with NF-E2 mutants to cells transduced with NF-E2 wt. *$p<0.05$, **$p<0.01$.

(C) Murine Bone Marrow Transplant Model. Donor bone marrow was transduced with lentiviruses encoding wt NF-E2 or the 248*aa*, the 263*aa* or the del297-300 mutant and transplanted into recipient mice.

(D) Peripheral Blood Analysis. Twelve weeks transplantation, hematocrit (HCT) and red blood cell (RBC) (top panels) as well as platelet (PLT) counts (bottom panel) were assayed for mice transplanted with wt NF-E2 or the 248*aa*, the 263*aa* or the del297-300 mutant.

Figure 12:
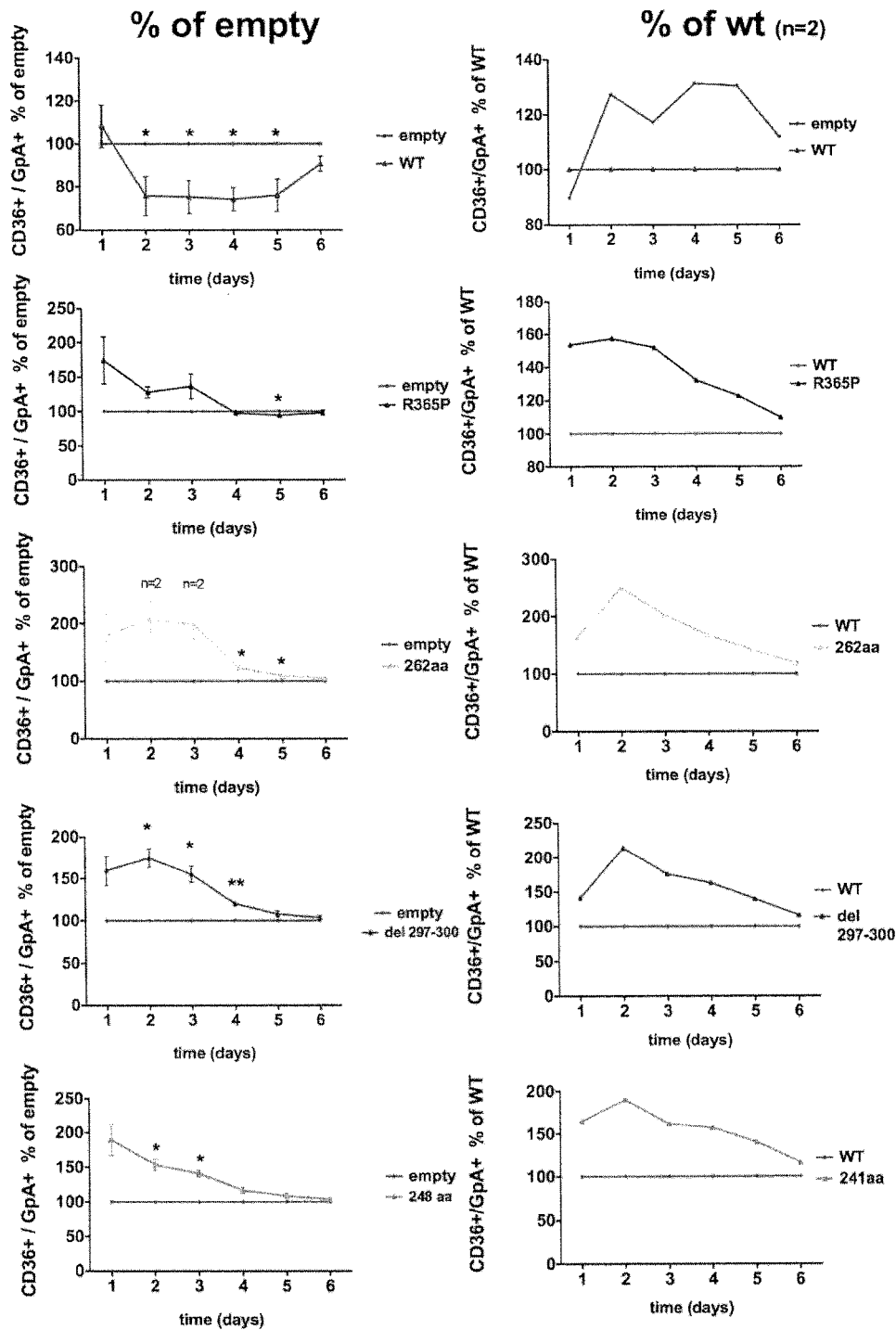

FIG. 12. Effect of NF-E2 on erythroid maturation.

The effect of the mutations compared with wild-type NF-E2 on the erythroid maturation depending on time is shown in FIG. 12.

Figure 13:
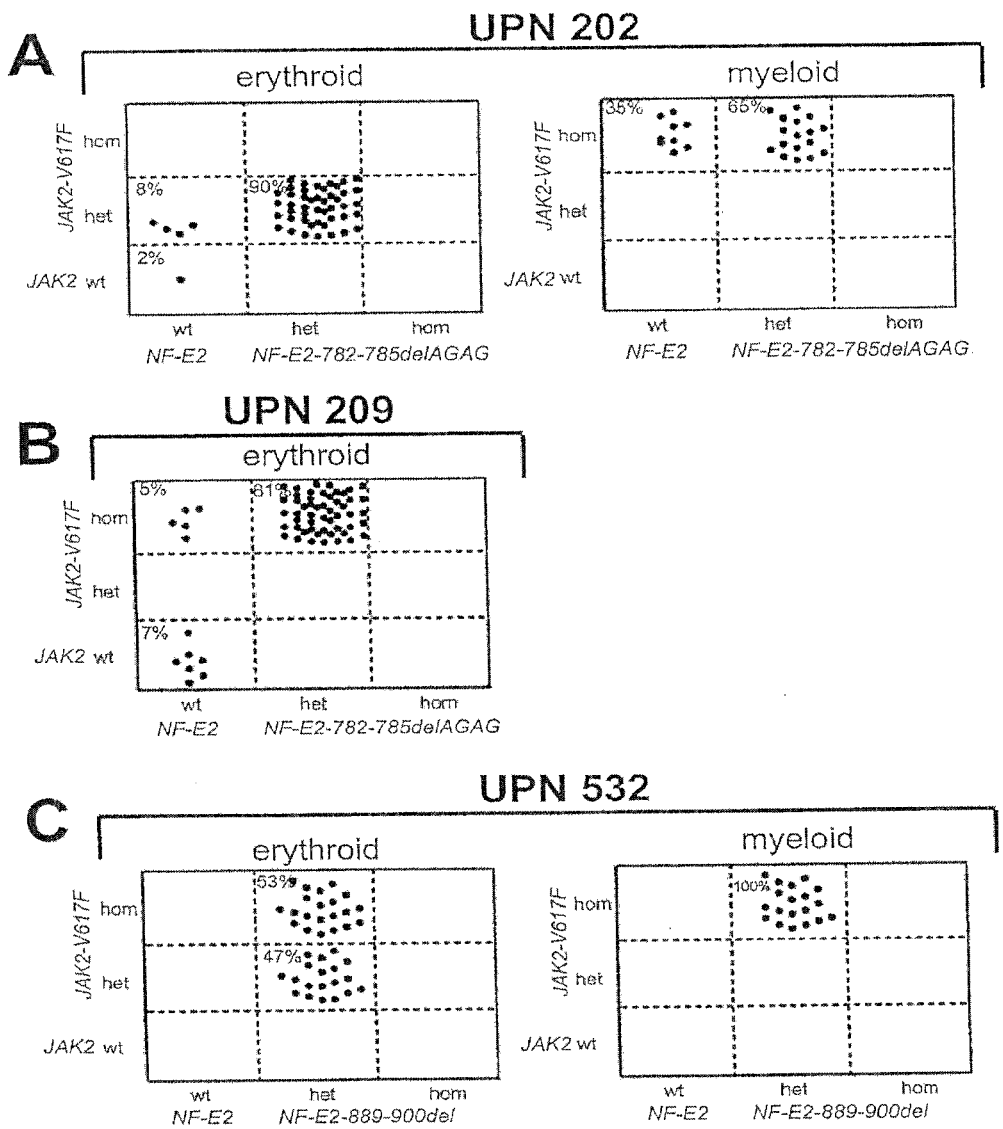
Figure 13:
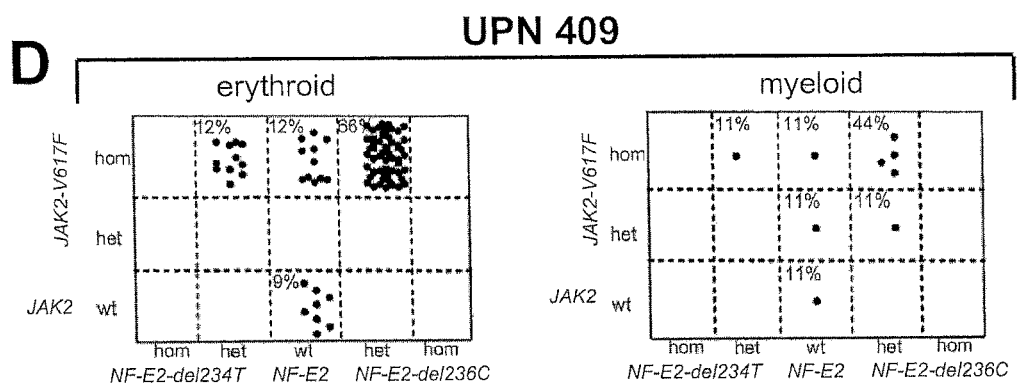

FIG. 13: Mutational analysis of hematopoietic colonies. Mononuclear cells of the MPN patients indicated were seeded in methylcellulose and individual colonies harvested after 14 days. Colonies were assays for presence of the JAK2$^{V617F}$ and the NF-E2 mutations by PCR amplification and sequencing. Genotypoes of the individual colonies, each represented by a single dot, are depicted. Individual hematopoietic colonies grown in methylcellulose of four different patients having the abbreviation UPN 202, 209, 409 and 532 were analyzed. In FIG. 13 the abbreviation "wt" means wild type, "het" means heterozygous and "hom" means homozygous.

DETAILED DESCRIPTION OF THE PREFERRED EMBODIMENTS

The diagnostic method of the present invention is an ex vivo or in vitro method which means that the method can be performed on a sample comprising a suitable nucleic acid. Such a sample can be obtained from blood, but the samples can alternatively also be obtained from other body fluids like bone marrow or from a biopsy of a solid tumor. Even saliva may be a suitable source of nucleic acid. The method allows the determination whether a mutation or a variation of the NF-E2 gene is detectable. The nature of the mutation or of the variant identified allows diagnosis of the disease the patient is suffering from.

A mutation according to the present invention means that the nucleic acid sequence as shown in SEQ ID NO:2 is changed which leads consequently to changes in the amino acid sequence of the mutated gene. Such a mutation may lead to a change of the amino acid sequence or even to a frame shift in the coding sequence which results in the creation of a stop codon having the consequence that the translational product of the mutated gene results in a shorter form of the NF-E2 gene product.

The term "variation" of the NF-E2 gene product is understood in the sense that the NF-E2 gene product differs from the wild-type amino acid sequence as shown in SEQ ID NO:1.

In a preferred embodiment of the present invention the method is performed by using the well-known PCR technology. Since the nucleic acid sequence coding for the wild-type NF-E2 gene is known (SEQ ID NO:2) the person skilled in the art can easily select suitable short sequences as primers for amplification of nucleic acids. The primer sequences consist of 10-30, preferably 12-28, more preferred 15-25 and especially preferred 18-22 consecutive nucleotides of the SEQ ID NO:2 or the complement thereof.

The forward primer is for example selected from SEQ ID NO:2 and the reverse primer is selected from the complementary strand to SEQ ID NO:2 which is known due to the general rules of base pairing. Usually forward and reverse primer cover a stretch of about 600 to 50, preferably 300 to 70, nucleotides, whereby the location of forward primer and reverse primer is selected in such a way that a short stretch of nucleic acid sequence is between the two primers.

In a preferred embodiment one of the primers is selected from an area between nucleotide 600 and 900, more preferred between nucleotide 700 and 800 of SEQ ID NO:2. The other primer required for PCR is selected from the strand complementary to this region.

The primers are usually completely complementary to the corresponding stretch shown in SEQ ID NO:2 or the complement thereof. It may, however, be considered to include one or two mispairings in order to improve the diagnostic efficiency of the PCR reaction.

After the primers have hybridized to the nucleic acid contained within the sample, hybridization and amplification of the nucleic acid strand takes place usually by using a heat-resistant polymerase. After sufficient cycles of polymerization a DNA fragment may be obtained which can be sequenced.

In another embodiment of the present invention the diagnostic method can be performed by using a quantitative PCR or a so-called real time PCR (RT-PCR). The real time PCR is used in order to determine nucleic acids quantitatively. By using primers which occur at stretches where mutations or variations of the nucleic acid sequence can frequently be expected it is possible to conclude from the reduced amount of the nucleic acid produced by PCR compared with the wild-type NF-E2 sequence whether a mutation is present or not.

In the course of the present invention the sequences of NF-E2 of different patients have been checked, whereby recurrent truncating mutations in NF-E2 were identified.

Seven different frameshift mutations, insertions and deletions, were detected in the NF-E2 coding sequence in 8 patients with myeloproliferative neoplasms (MPNs), 3 with polycythemia vera (PV) and 5 with myelofibrosis, either primary myelofibrosis (PMF) or secondary, post-MPN myelofibrosis (sMF). Two mutations, c.782-785delAGAG and c.622_623 insG, were found in two different patients each, while one patient harbored two separate mutations.

TABLE 1

NF-E2 Mutations detected in MPN patients.

| Patient number* | Diagnosis | variant cDNA NM_006163.1 | variant protein | JAK2V617F | genetics |
|---|---|---|---|---|---|
| F-209 | PV | c.782-785delAGAG | p.E261AfsX3 | positive | acquired |
| F-2836 | postET-PMF | c.622insG | pE221GfsX7 | n.d. | |
| MPD-241 | postPV-PMF | c. 732_733insG | p.L245VfsX5 | positive | |
| F-202 | PV | c.782-785delAGAG | p.E261AfsX3 | positive | acquired |
| U-409 | PV | c. 236delC c.234delT | p.P79LfsX32 p.P79LfsX32 | positive | acquired acquired |
| U-532 | PMF | c889_900del | p.E297-R300del | positive | acquired |
| U-980 | Post-ET-PMF | c.780_781insA | p.E261RfsX44 | positive | acquired |
| U-442 | post-PV-PMF | c.622insG | p.E221GfsX7 | positive | |

Table 1 shows NF-E2 Mutations detected in MPN patients. The location of the detected mutation is shown with regard to the cDNA contained in SEQ ID NO:2. Moreover, a correlation between diagnosis of the disease and mutation can be seen.

The frameshifts introduce premature stop codons in the open reading frame, leading to truncations in the NF-E2 protein (FIG. 8A). One 12 bp deletion, c.889-900del, causes an in-frame deletion of 4 amino acids, which includes the N-terminal leucine, of the leucine zipper heterodimerization domain.

Insertion and deletion mutations in NF-E2 were detected exclusively in PV and PMF patients (3 of 144 patients; 2.1% and 5 of 192 patients; 2.7% respectively, Table 2), not in healthy controls. This allows a diagnosis of a myeloproliferative neoplasm (MPN) and therefore enables the clinically important discrimination between the diagnosis of an acquired myeloprolifertive disorder, distinguishing it from a physiological reactive process. More details and clinical characteristics of the patients can be seen from Table 2.

It has been found that two specific mutations having the abbreviation c.622insG and p.E221GfsX7 which are shown in SEQ ID NO:8 could also be detected in a patient suffering from myelodysplastic syndrome (MDS) who later transformed to acute myeloic leukemia (AML). This patient had the identification number UPN:N-022. Therefore, the method disclosed herein can also be used to identify and diagnose patients with myelodysplastic syndromes, with acute myeloid leukemia as well as with solid tumors, which are frequently molecularly related to hematologic diseases. For example, the mutations IDH1 and IDH2 could be detected with patients suffering from AML (acute myeloid leukemia) as well as in patients suffering from glioblastomas.

By detecting mutations in the NF-E2 gene, reactive processes can be excluded which can often be extremely difficult to distinguish from neoplastic processes without molecular markers such as the NF-E2 mutations.

In general it can be said that when an NF-E2 mutation can be detected according to the method disclosed herein, a secondary erythrocytosis, a secondary thrombocytosis or a reactive leukocytosis can be excluded.

The method of the present invention can also be used for monitoring the disease and the effectiveness of the therapeutic treatment. The patient is treated according to the best suitable therapy and it can be monitored by the method of the present invention whether the therapy shows the desired therapeutic success.

TABLE 3

Age at Diagnosis of MPN Patients with and without NF-E2 mutations and sequence variations.

| Diagnosis | Genotype | Number of Patients | Age at Diagnosis | Significance |
|---|---|---|---|---|
| PV | wt | 141 | 55 | |
| | NF-E2 mutations | 3 | 55 | |
| | NF-E2 variants (all) | 6 | 51 | |
| | NF-E2 R365P only | 2 | 39 | *p < 0.05 |
| PMF | wt | 187 | 57 | |
| | NF-E2 mutations | 5 | 63 | |
| | NF-E2 variants (all) | 4 | 51 | |
| | NF-E2 R365P only | 4 | 51 | |
| PV + PMF | wt | 328 | 56 | |
| | NF-E2 mutations | 8 | 60 | |
| | NF-E2 variants (all) | 10 | 52.2 | |
| | NF-E2 R365P only | 6 | 46.2 | *p < 0.05 |
| ET | wt | 118 | 49 | |
| | NF-E2 mutations | 0 | | |
| | NF-E2 variants (all) | 2 | 57 | |
| | NF-E2 R365P only | 0 | | |

NF-E2 sequence variations were observed in 1.7% of ET (2 out of 120 patients), 4.2% of PV (6 out of 144) and 2.1% of PMF patients (4 out of 192 patients). Again, the majority of the variants were present exclusively among MPN patients, PV (n=144), PMF (n=192) and ET (n=120), but not in healthy controls. Of the seven SNPs, the most frequently observed was a G to C transversion at by 1094, leading to an argenine to proline substitution at amino acid 365 of the NF-E2 protein (R365P). This change was observed in 2 PV patients (out of 144=1.4%) and 4 PMF patients (out of

TABLE 2

Clinical Characteristics of the MPN MDS, sAML and CMML Patients Studied.

| Diagnosis | Number of patients | Gender m/f | Age at diagnosis in years mean (range) | Duration of disease in years mean (range) | Hemoglobin (at sample) | WBC (at sample) | Platelets (at sample) |
|---|---|---|---|---|---|---|---|
| ET | 120 | 55/65 | 49.7 (17.3-82.3) | 4.9 (0.0-21.5) | 14.1 (8.6-33.9) | 8.1 (2.5-31.4) | 671 (149-2393) |
| PV | 144 | 71/73 | 55.5 (16.7-78.4) | 5.3 (0.0-29.3) | 14.6 (7.9-20.3) | 15.2 (1.8-209.0) | 513 (40-2055) |
| PMF | 192 | 102/90 | 56.9 (21.3-86.4) | 3.5 (0.0-20.5) | 10.7 (1.2-17.2) | 15.1 (0.8-102.1) | 292 (99-593) |
| MPN-U | 49 | | | | | | |
| MDS | 57 | | | | | | |
| sAML (post-MPN) | 39 | 21/18 | 57.0 (42.2-76.0) | 7.0 (0.0-20.9) | 9.7 (6.9-15.5) | 39.2 (1.5-182.4) | 83 (11-362) |
| CMML | 67 | | | | | | |

Abbreviations used and data displayed:
Diagnosis:
Polycythemia vera (PV),
Essential Thrombocythemia (ET),
Primary Myelofibrosis (PMF);
Gender:
male (m),
female (f);
Age at Diagnosis: mean (range);
Duration of Disease: mean, (range);
White Blood Cell count (WBC), mean (range),
Hematocrit (Hct), mean (range);
Platelets (Plt), mean (range).
CBC at the time the blood sample was obtained.

Constitutive DNA, obtained from buccal swabs, was available from 4 patients and in all cases, we were able to demonstrate that the mutations were acquired (Table1).

Novel NF-E2 sequence variants (SNPs) were also detected.

In addition to the insertion/deletion mutations, seven different sequence variants not corresponding to known NF-E2 SNPs (Table 3) were observed.

192=2.2%). Buccal swab DNA samples from three patients showed that this variant was constitutively present in these individuals.

Interestingly, this SNP is only found in 0.3% of the general population (n=4550; NCBI SNP Database, http://www.ncbi.nlm.nih.gov/projects/SNP/snp_ref.cgi?rs=141251053), and is therefore statistically highly significantly enriched in MPN patients, especially in patients with PMF (p<0.0001, Chi-Square Test).

A loss of DNA binding and transactivation potential has been observed in NF-E2 mutants.

Because the truncated NF-E2 proteins contain neither the DNA binding domain nor the leucine zipper required for dimerization to small Maf proteins (compare with FIG. 8A), it was investigated whether truncated NF-E2 mutants retain DNA binding activity in an electrophoretic mobility shift assay (EMSA). NF-E2 requires interaction with a small Maf protein, here MafG, in order to bind DNA (FIG. 8B, compare lane 2 and lane 4). Specificity of the NF-E2/MafG heterodimer binding to its cognate DNA sequence was verified by competition and super-shift experiments (FIG. 8B, lanes 5-8). In contrast to wt NF-E2, the two truncated NF-E2 mutants (p.L245VfsX5, here called 248aa, and p.E261AfsX3, here called 236 aa) were unable to bind DNA even in the presence of MafG (FIG. 8B, compare lanes 9, 10 and 12). Furthermore, the NF-E2 mutant carrying the 4 aa deletion, here called del297-300, was likewise unable to bind DNA (FIG. 8B, compare lanes 9 and 13). In contrast, the NF-E2 R365P variant retained DNA binding activity (FIG. 8B, compare lanes 9, and 11). Protein expression of all mutants was verified by Western Blotting (FIG. 8C).

Subsequently, it was investigated whether the NF-E2 mutants retained transactivation potential in reporter gene assays. Two different reporter gene constructs were used, one containing a known NF-E2 binding site from the beta-globin promoter (Igarashi et al.), and a second containing a NF-E2 binding site in the beta1-tubulin promoter. Both reporter constructs yielded similar results (FIGS. 9A and B); all three NF-E2 mutants tested were no longer able to evoke reporter gene activity above the background levels observed with MafG alone.

Because transcription of a plasmid DNA does not reflect physiological conditions within the chromatin bound DNA, CB3 cells were used to test the mutants under physiological conditions. CB3 cells carry a homozygous viral insertion in the NF-E2 locus and therefore express neither NF-E2 nor its target beta-globin. Upon re-introduction of NF-E2, beta-globin is robustly expressed. We introduced wt NF-E2 or two truncation mutations, 248aa and 263 aa, as well as the 4aa deletion, del 297-300, into CB3 cells and measured beta-globin mRNA expression by qRT-PCR. While transduction of wt NF-E2 caused a 100-fold increase in beta-globin mRNA expression, all three NF-E2 mutants were unable to activate beta-globin expression (FIG. 9C).

NF-E2 mutants and variants display a gain of function.

Because all the NF-E2 mutations were observed in a heterozygous state, hence unfold their effect in the presence of wt NF-E2, the effect of co-expression of wt NF-E2 and NF-E2 mutants in CB3 cells was investigated. CB3 cells stably transfected with wt NF-E2 were infected with an empty pLeGO-iT virus, or viruses expressing the two truncation mutants, 248 aa and 263 aa, the 4aa deletion, del 297-300, and assayed for beta-globin expression (FIGS. 10A and B). While transduction with empty pLeGO-iT had no effect on beta-globin mRNA expression in NF-E2 wt expressing CB3 cells (FIG. 10B), transduction with the three mutants, which on their own retain no transactivation activity (FIG. 9C), enhance wt NF-E2 activity between 3 and 8-fold, with the del297-300 mutant displaying the strongest effect (FIG. 10B). Thus, while unable to transactivate transcription on their own, the NF-E2 mutants have gained a neomorphic function which significantly enhances wt NF-E2 activity.

Because of the observed enhancement of beta-globin expression the effect of NF-E2 mutants on erythroid maturation of healthy CD34+ hematopoietic stem cells was examined. It has previously been shown that overexpression of wt NF-E2 delays erythroid maturation in a liquid culture system promoting erythroid maturation.

Purified peripheral blood CD34+ cells from healthy donors were transduced either with empty lentivirus or with lentiviruses expressing wt NF-E2, the del297-300, the 248aa or the 263aa mutation. The change of the markers from CD34+ to CD36/glycophorin A reflects the change to erythroid progenitor cells. Transduced cells were purified by FACS, cultured and monitored daily for erythroid maturation by staining for CD36 and glycophrin A (GpA) (FIG. 11A). The proportion of erythroid cells, doubly positive for CD36 and GpA, is decreased in NF-E2 wt expressing cells compared to empty vector transduced controls (FIG. 11B, top). Compared to NF-E2 wt transduced cells, the three mutants promote faster erythroid maturation (FIG. 11B, right panels). This observation would be compatible either with a loss of NF-E2 wt function, or with a gain of function. Importantly, all three mutants accelerate erythroid maturation compared to empty virus transduced cells, witnessed by the earlier appearance of larger proportions of CD36/GpA double positive erythroid cells (FIG. 11B, left panels). These data provide strong evidence for a gain-of-function by the NF-E2 mutants, one that promotes erythroid maturation.

It has been found that NF-E2 mutations confer a proliferative advantage in the context of the JAK2$^{V617F}$ mutation MPN patients carrying NF-E2 mutations were also tested for presence of the JAK2$^{V617F}$ mutation. All seven patients assayed carried both a NF-E2 mutation and the JAK2$^{V617F}$ mutation (Table 1). Analysis of individual hematopoietic colonies grown in methylcellulose revealed that in two patients, 202 and 209, the NF-E2 mutation was acquired subsequent to the JAK2$^{V617F}$ mutation (FIG. 13), as some colonies carrying only the JAK2$^{V617F}$ mutation but not the NF-E2 mutation were found and all colonies positive for the NF-E2 mutation also carried JAK2$^{V617F}$. Interestingly, these assays revealed a proliferative advantage of cells carrying the NF-E2 mutation over cells carrying only JAK2$^{V617F}$ either in the context of a heterozygous (patient 202) or a homozygous JAK2$^{V617F}$ mutation (patient 209; FIG. 13). In both patients, cells carrying both the NF-E2 mutation and the JAK2$^{V617F}$ mutation represent the vast majority (90 and 81%, respectively), of the colonies analyzed, demonstrating that the JAK2$^{V617F}$-positive cell that acquired the NF-E2 mutation outcompeted cells carrying the JAK2$^{V617F}$ mutation alone.

In patient 532, it cannot be determined for sure whether the NF-E2 or the JAK2$^{V617F}$ mutation was incurred first. However, again, the presence of both mutations clearly provided a proliferative advantage over either of the mutations alone, as all colonies carry both mutations. In addition, in the context of a NF-E2 mutation, as in wt NF-E2 patients, homozygous JAK2$^{V617F}$ cells outgrow heterozygous JAK2$^{V617F}$ cells.

A second patient, 409, has acquired two separate and mutually exclusive NF-E2 mutations, c.236delC and c.234delT (FIG. 13D and Table 1). The vast majority of both myeloid and erythroid colonies (>89%; n=y) carry a homozygous JAK2$^{V617F}$ mutation. However, 65% of the erythroid and 50% of the myeloid colonies carry the c.236delC while 12% of the erythroid and 28% of the myeloid colonies carry a c.234delT mutation (FIG. 13D). The remainder of the colonies are wt for NF-E2, demonstrating that both mutations are acquired and again suggesting that both NF-E2 mutations confer a growth advantage, as they outcompete the NF-E2 wt cells.

It could be shown that NF-E2 mutants cause polycythemia and thrombocytosis in a murine BMT model.

In order to test whether the NF-E2 mutant promote erythroid maturation in vivo, a murine bone marrow transplant model was used. Donor bone marrow was transduced with lentiviruses encoding NF-E2 wt or the 248aa, the 263aa or the del297-300 mutants and transplanted into recipient mice (FIG. 11C). Donor engraftment exceeded 95% in all mice. Twelve weeks after transplantation, peripheral blood was analyzed. Compared to mice transplanted with wt NF-E2, which, similar to NF-E2 transgenic mice, display normal hematocrit and normal RBCs, mice transplanted with two of the three NF-E2 mutants displayed a significant elevation in hematocrit and in RBC number and this trend was evident in the third mutant as well (FIG. 11D, top panels). In addition, while NF-E2 wt transplanted mice, like NF-E2 tg mice, display normal platelet values at 3 months, mice transplanted with all three mutants displayed a statistically significant elevation in platelet number (FIG. 11D, bottom panel). These data demonstrate that presence of the NF-E2 mutants is sufficient to cause erythrocytosis and thrombocytosis in a murine model.

Sequence Listing Details:

The sequence listing comprises the relevant sequences whereby the numbers designate the following sequences:

| | |
|---|---|
| SEQ ID NO: 1 | amino acid sequence of wild-type NF-E2 |
| SEQ ID NO: 2 | DNA sequence coding for wild-type NF-E2 |
| SEQ ID NO: 3 | cDNA sequence coding for the mutated protein F-209 of FIG. 2 |
| SEQ ID NO: 4 | amino acid sequence coding for the mutated protein F-209 of FIG. 2 |
| SEQ ID NO: 5 | cDNA sequence coding for the mutated protein MPD-RC-241 of FIG. 3 |
| SEQ ID NO: 6 | amino acid sequence coding for the mutated protein MPD-RC-241 of FIG. 3 |
| SEQ ID NO: 7 | cDNA sequence coding for the mutated protein F-2836 of FIG. 4 |
| SEQ ID NO: 8 | amino acid sequence coding for the mutated protein F-2836 of FIG. 4 |
| SEQ ID NO: 9 | cDNA sequence coding for the mutated protein U-532 of FIG. 5 |
| SEQ ID NO: 10 | amino acid sequence coding for the mutated protein U-532 of FIG. 5 |
| SEQ ID NO: 11 | cDNA sequence coding for the mutated protein U-409 of FIG. 6 |
| SEQ ID NO: 12 | amino acid sequence coding for the mutated protein U-409 of FIG. 6 |
| SEQ ID NO: 13 | cDNA sequence coding for the variant U-980 of FIG. 7 |
| SEQ ID NO: 14 | amino acid sequence coding for the variant U-980 of FIG. 7 |
| SEQ ID NO: 15 | primer sequence |
| SEQ ID NO: 16 | primer sequence |
| SEQ ID NO: 17 | probe sequence |
| SEQ ID NO: 18 | primer sequence |
| SEQ ID NO: 19 | primer sequence |
| SEQ ID NO: 20 | primer sequence |
| SEQ ID NO: 21 | primer sequence |
| SEQ ID NO: 22 | primer sequence |
| SEQ ID NO: 23: | primer sequence |
| SEQ ID NO: 24: | primer sequence |
| SEQ ID NO: 25 | primer sequence |

EXAMPLES

Example 1

MPN Patients and Healthy Controls

Peripheral blood samples were obtained from PV (n=144) ET (n=120) and PMF patients (n=192), fulfilling the WHO criteria for diagnosis. Additional samples were obtained from the Tissue Bank of the Myeloproliferative Disease Research Consortium (MPD-RC), which uses the same diagnostic criteria. Patient characteristics are summarized in Table 2. Buffy coats of healthy volunteer blood donors were obtained from the University Hospital Freiburg Center for Blood Transfusion Nijmegen. Isolated granulocytes were obtained by dextran sedimentation and Ficoll gradient centrifugation as described by Temerinac et al. [Blood 95 (2000), pp 2569-2576] and used for DNA preparation and subsequent NF-E2 sequence analysis.

Buccal swabs were used to obtain DNA for germline analysis. The study protocol was approved by the local ethics committees (University Hospital Freiburg, University Hospital Ulm, as well as the Member Institutions of the MPD-RC) and informed consent was obtained from all patients. Each patient was assigned a unique patient number (UPN), which was used thereafter for the protection of privacy. All patients were tested for the presence of the $JAK2^{V617F}$ mutation by qRT-PCR or LNA PCR as described by Steimle et al. [Ann. Hemathol. 86 (2007), pp 239-244]. The results of the experiments can be seen from the figures.

Example 2

NF-E2 Sequencing

Exons 2 and 3 of the NF-E2 locus were amplified by PCR and subjected to direct sequencing according to standard protocols. Primer sequences and reaction conditions were as follows:

```
Primer für PCR and CSR:
Exon 2:
Forward:
                                  SEQ ID NO: 18
CGGTCTCTCCTTCCCTCAGGGGA Reverse:
                                  SEQ ID NO: 19
TCTTCTCCGACACACGGCCTCC Exon 3A
Forward:
                                  SEQ ID NO: 20
TGCGACTTTCAGAAGAATCCAGCTTG Reverse:
                                  SEQ ID NO: 21
TGGAGTGGGCCAAGGAGTTGGG Exon 3B
Forward:
                                  SEQ ID NO: 22
TCGGCGGCGCAGCGAATATG Reverse:
                                  SEQ ID NO: 23
GTAGCTGTTGCCTGATTCATCCCG Exon 3C
Forward:
                                  SEQ ID NO: 24
GAGGTCATGCGCCAACAGCTGAC Reverse:
                                  SEQ ID NO: 25
TGCTCAGCCTCAAGCCCAAATTTT
```

For each amplification the following reaction mixture was prepared:
PCR-Mastermix:

| μl | 1x-Mix | |
|---|---|---|
| 18.25 | dd H$_2$O | |
| 2.5 | Puffer | |
| 0.75 | MgCl$_2$ | |
| 0.25 | dNTPs | 0.25 mM Fa. Roche |
| 0.5 | Primer F | 10 pmol/μl Fa. MWG |
| 0.5 | Primer R | |
| 0.25 | Platinum Taq | Fa. Invitrogen |

23 μl PCR Mastermix and 1 μl DNA was amplified under the following conditions:
PCR-Conditions:

| 94° C. | 5 min | |
|---|---|---|
| 94° C. | 30 sec | |
| 60° C. | 30 sec | 30x repeated |
| 72° C. | 1 min | |
| 72° C. | 10 min | |
| 4° C. | ∞ | |

For RT-PCT the Following CSR-Mastermix was Used:

| μl | 1x-Mix | |
|---|---|---|
| 10 | dd H$_2$O. | |
| 2 | BigDye 1.1 | Fa. Applied Biosystems |
| 1 | sequencing buffer | Fa. Applied Biosystems |
| 1 | Primer F oder R | 10 pmol/μl |
| | 14 μl + 1 μl purified PCR-product | |

The CSR-Conditions were as Follows:

| 96° C. | 2 min | |
|---|---|---|
| 95° C. | 15 sec | |
| 55° C. | 1 min | 25X repeated |
| 60° C. | 3 min | |
| 4° C. | 10 min | |
| 4° C. | ∞ | |

Example 3

Electrophoretic Mobility Shift Assay (EMSA) Analysis 293 nuclear extracts were prepared as described by Schreiber et al. [Nucleic Acid Res. 17 (1989), pp 6419]. In brief, 1-2 μg of nuclear extracts were added to a binding reaction containing 2 μg poly dl-dC, 2 μl 10× binding buffer (10 mM HEPES, Ph: 7.9, 5 mM MgCl$_2$, 30 mM KC, 1 mM EDTA, 1 mM dithiothreitol, 12% glycerol), and 0.5 ng of $^{32}$P-labeled oligonucelotide. The oligonucleotide containing the NF-E2 consensus binding site at bp-160 of the human porphobilinogen deainase gene promoter [Mignotte et al., PNAS 86 (1989), pp 6548-52] was synthesized by Eurofins MWG Operon (Ebersberg, Germany) and the NF-κB consensus oligonucleotide was purchased from Promega (Mannheim, Germany). When indicated, either a 100-fold excess of non-radiaoactive oligonucleotide, a NF-E2 antibody (HPA001914, Sigma-Aldrich, St. Louis, Mo.) or a NF-κB p65 antibody (SC-372, Santa Cruz Biotechnologies, Santa Cruz, Calif.) were added. The reaction was incubated at RT for 15 min. For supershift assays, extracts and antibodies were pre-incubated for 10 minutes at RT prior to addition of the radioactive nucleotide. The results of the experiment are summarized in FIG. 8.

Example 4

Immunoblotting 293 cells, transduced with expression vectors encoding NF-E2 wt or mutants, were lysed in SC buffer (50 mM Tris/HCl pH 8.0; 170 mM NaCl; 0.1% (v/v) NP40; 50 mM NaF; 2 mM Na3VO4; 0.2 mM DTT; 20% (v/v) glycerol; 1 μg/ml BSA) supplemented with 1× Complete® (Roche, Mannheim, Germany). Cell lysates were subjected to SDS-PAGE-gel-electrophoresis and Western Blotting. The primary antibody against NF-E2 was used as described in Goerttler et al. The blots were stripped and reprobed against β-Actin (4967, Cell Signaling Technologies, Danvers, Mass.) or GAPDH (G8795, Sigma, Germany) to control for equal loading. The immunocomplexes were detected using chemiluminescence Western Blotting Reagents (GE Healthcare, Freiburg, Germany).

Example 5

Plasmids: NF-E2 Reporter Constructs and Lentiviral Vectors

A 5.2 kb region, spanning bp-1 to bp-5221 of the betel tubulin gene, was amplified by PCR from human genomic DNA and inserted into the pGL3basic *luciferase* reporter vector (Promega, Mannheim, Germany) resulting in the β1-tubulin −5.2 kb-luc construct.

The pRBGP2-*Luciferase* (pRBGP2-Luc) reporter plasmid (described by Igarashi et al.), which contains three copies of the NF-E2 binding site from the chicken beta-globin enhancer in a TATA-*luciferase* reporter vector, was a kind gift of Masayuki Yamamoto (Tsukuba University, Tsukuba, Japan).

Insertion and deletion mutations detected in MPN patients were inserted into the NF-E2 cDNA by site directed mutagenesis using the GeneTailor site-directed mutagenesis system (Invitrogen). Wt and mutant NF-E2 cDNA was cloned into pLEGO-iG, pLEGO-iT2 and pRc/CMV vectors by restriction enzyme digestion. The MafG-pCMV6-XL4 expression vector was purchased from Origene.

Example 6

Transient Transfections and *Luciferase* Assays 293 cells were transiently transfected with 0.2 μg of either the pRBGP2-Luc or the beta1-tubulin-*Luciferase* reporter gene construct, together with 1.36 μg of either pRc/CMV-NF-E2 wt or a pRc/CMV-NF-E2 mutant expression vector or the pRc/CMV empty control vector as well as 0.34 μg of a MafG-pCMV6-XL4 expression vector (Origene). In addition 0.1 μg of a TK-*Renilla* plasmid (Promega, Mannheim, Germany) were co-transfected as an internal control.

Cells were harvested 16 hours post transfection, and *luciferase* activity was determined using the Dual *Luciferase* Reporter Assay System (Promega). *Luciferase* activity was normalized to the *Renilla* internal control to compensate for variations in transfection efficiency.

Example 7 a) Lentiviral Transductions

CB3 cells, a kind gift of Dr. V. Blank, were transduced with either empty pLeGO-iG or pLeGo-iG containing wtNF-E2 or mutants and variants thereof as described by Roelz et al. [Exp. Hematol. 38 (2010), pp 792-7] using MOIs between 1 and 8. GFP expressing cells were sorted to obtain pure populations.

CB3-NF-E2 wt cells were obtained by transducing CB3 cells with pLeGO-iG-wt-NF-E2, and subsequently cloning single transduced cells by limiting dilution. A stable clone was selected and used for co-expression of NF-E2 mutants and variants. CB3-NF-E2 wt cells were transduced with either pLeGO-iT2 containing mutant and variant NF-E2 cDNAs or the empty control vector using MOIs between 0.5 and 9. Tomato expressing cells were sorted to obtain pure populations.

Lentiviral transduction of peripheral blood CD34+ cells from healthy donors using pLEGO-iG expressing wt or mutant NF-E2 was performed as described by Roelz et al. [Exp. Hematol. 38 (2010), pp 792-7]. Briefly, cells were prestimulated for 12 hours in serum-free medium (StemSpan SFEM, 09650, Stem Cell Technologies, Vancouver, BC, Canada) containing 100 ng/ml rhSCF (300-07, PeproTech, Rocky Hill, N.J.), 100 ng/ml rhFLT-3 ligand (300-19, PeproTech) as well as 20 ng/ml each rhIL6 (200-06, PeproTech) and rhTPO (300-18, PeproTech). Subsequently, CD34+ cells were subjected to two cycles of lentiviral infection over a 48 hour period using MOIs of 10 without the addition of a transduction facilitator. GFP expressing cells were FACS sorted to obtain pure populations.

B) Erythroid Differentiation Medium

Erythroid differentiation medium consisted of StemSpan SFEM (09600, StemCell Technologies, Vancouver, BC, Canada) supplemented with 50 ng/ml rhSCF (300-07, PeproTech, Rocky Hill, N.J.), 1 IU/ml EPO (Erypo FS 4000, Ortho Biotech, Bridgewater, N.J.), 50 IU/ml rhIL-3 (200-03, PeproTech), 40 ng/ml Human Low Density Lipoprotein (4004, Harbor Bio-Products, Norwood, Mass.), 100 IU/ml Penicillin, 100 mg/ml Streptomycin (DE17-602E, Cambrex, North Brunswick, N.J.) and 2 µl/ml Primocin (VZA-1021, Amaxa Biosystems, Cologne, Germany). Cells were maintained at a concentration of $2 \times 10^5$/ml.

c) FACS Analysis

CD34+ cells were stained with a phycoerythrin (PE)-conjugated anti-CD235a/GpA antibody [clone GA-R2 (HIR2)] as well as an allophycocyanin (APC)-conjugated anti-CD36 antibody (clone CB38) both from BD Biosciences, Franklin Lakes, N.J., USA and evaluated on a FACS Calibur (BD Biosciences). Data were analysed using the FlowJo software (FlowJo, Ashland, Oreg., USA).

The results of the transduction experiments are shown in FIG. 11 and FIG. 12.

D) Colony Assays

Cells were seeded in methylcellulose media (1000 cells/ml) containing SCF, IL-3, granulocyte-macrophage colony-stimulating factor (GM-CSF) and EPO (H4434; Stem Cell Technologies) and incubated for 14 d at 37° C., 5% $CO_2$. Erythroid colony-forming units (CFU-E) were scored on day 8 and erythroid burst-forming units (BFU-E) as well as granulocytic/macrophage colony-forming units CFU-GM were scored on day 14. Colonies were counted by independent observers, blinded to the experimental conditions.

E) Data Analysis

Paired or unpaired Student t-tests (two sided or one sided) and the Mann-Whitney Rank sum test were used to determine whether a significant ($p<0.05$) difference existed between two groups. When comparing more than two groups, a One Way ANOVA was used. These analyses were performed using the SigmaPlot 11.0 (Systat, Erkrath, Germany) or the GraphPad Prism 5.0 software (www.graphpad.com).

Example 8

Quantitative RT-PCR Assays

Quantitative RT-PCR measurements were performed using an Assay on Demand (Mm01611268_g1 Hbb-b1, Applied Biosystems) for analysis of murine beta-globin as well as the following primer and probe sequences for murine R-2-Microglobulin:

```
FP:
                                    (SEQ ID NO: 15)
5' TCT TTC TGG CCT GGA GGC TAT C 3'

RP:
                                    (SEQ ID NO: 16)
5' TGC TGG ATG ACG TGA GTA AAC C 3'

TaqMan Probe:
                                    (SEQ ID NO: 17)
6FAM-AGC GTA CTC CAA AGA T-MGBNFQ
```

Reverse transcription of total CB3 cell RNA was performed using the TaqMan Reverse Transcription Kit (Applied Biosystems). Q-PCR assays were performed in duplicate in an ABI PRISM 7000 Cycler and analyzed using the ABI PRISM 7000 software. Beta globin expression was determined relative to expression of the β-2-Microglobulin house-keeping gene using the ΔΔCt method.

The invention claimed is:

1. An ex vivo or in vitro method for diagnosing an acquired myeloid neoplasm or solid tumor in a human patient, said method comprising the steps of:
   a) isolating by means of a PCR process a nucleic acid containing a mutant or variant form of the NF-E2 gene from a blood, bone marrow, or solid tumor biopsy sample obtained from said patient, further wherein said PCR process includes a hybridization step with at least one labeled primer having a nucleic acid sequence selected from the group consisting of SEQ ID NOs: 18-25;
   b) detecting the presence of mutant or variant form of the NF-E2 gene in said sample by obtaining the nucleic acid sequence of the nucleic acid isolated in step a) and:
      i. comparing the nucleic acid sequence obtained in step a) to the nucleic acid sequence of SEQ ID NO: 2, or
      ii. comparing an amino acid sequence corresponding to the nucleic acid sequence obtained in step a) to the amino acid sequence of SEQ ID NO:1, wherein any difference observed in steps b)(i) or b)(ii) indicates that said patient carries a mutant or variant form of the NF-E2 gene; and
   c) diagnosing said patient with a solid tumor or myeloid neoplasm selected from the group consisting of a myeloproliferative neoplasm (MPN), myelodysplastic syndrome (MDS), and acute myeloid leukemia (AML) when detection step b) reveals that said patient carries a mutant or variant form of the NF-E2 gene that codes for a mutant or variant NF-E2 protein having an amino acid sequence selected from the group consisting of SEQ ID NOs: 4, 6, 8, 10, 12, and 14.

2. The method according to claim 1, wherein said PCR process comprises a real time PCR reaction.

3. The method according to claim 1, wherein the myeloid neoplasia is a myeloproliferative neoplasm (MPN).

4. The method according to claim 3, wherein the myeloproliferative neoplasm (MPN) is selected from the group consisting of polycythemia vera (PV), essential thrombocythemia (ET) and myelofibrosis (MF).

5. The method according to claim 1, further comprising the steps of (d) administering to said patient a therapeutic regimen suitable for treating said myeloid neoplasm and (e) repeating said method at regular time intervals in order to monitor the effectiveness of said therapeutic regimen of step (d), further wherein the presence of any one of the mutant or variant forms of the NF-E2 gene set forth in step (c) in a blood, bone marrow, or solid tumor biopsy sample obtained from said patient subsequent to the administration of the therapeutic regimen of step (d) is indicative of therapeutic failure.

6. The method of claim 1, further wherein detection of any one of the mutant or variant forms of the NF-E2 gene set forth in step (c) serves to exclude a diagnosis of a physiological reactive process selected from the group consisting of a secondary erythrocytosis, a secondary thrombocytosis or a reactive leukocytosis in said patient.

7. An ex vivo or in vitro method for diagnosing, treating and assessing the progress of an acquired myeloid neoplasm or solid tumor in a human patient using a mutant or variant form of NF-E2 as an index of the disease state, said method comprising the steps of:
   a. isolating by means of a PCR process a nucleic acid containing a mutant or variant form of the NF-E2 gene in a blood, bone marrow, or solid tumor biopsy sample obtained from said patient, wherein said PCR process includes a hybridization step with at least one labeled probe or primer comprising 10 to 30 consecutive nucleotides of a nucleic acid selected from the group consisting of SEQ ID NOs: 3, 5, 7, 9, 11, and 13, further wherein said labeled probe or primer is capable of hybridizing with a truncated form of the NF-E2 protein set forth in SEQ ID NO: 1 that lacks either or both of (a) a DNA-binding domain comprising amino acids 263-287 of SEQ ID NO: 1, or (b) a leucine zipper domain comprising amino acids 294-339 of SEQ ID NO: 1 to give rise to a PCR amplification product;
   b. assaying the nucleic acid sequence isolated in step (a) for the presence of a mutant or variant form of the NF-E2 gene that codes for a mutant or variant NF-E2 protein having an amino acid sequence selected from the group consisting of SEQ ID NOs: 4, 6, 8, 10, 12, and 14;
   c. diagnosing said patient with a solid tumor or myeloid neoplasm selected from the group consisting of a myeloproliferative neoplasm (MPN), myelodysplastic syndrome (MDS), and acute myeloid leukemia (AML), when detection step b) reveals that said patient carries said mutant or variant form of the NF-E2 gene that gives rise to a truncated form of the NF-E2 protein that lacks either or both of said DNA-binding domain or said leucine zipper domain;
   d. administering to said patient a treatment specific for a myeloproliferative neoplasm (MPN), myelodysplastic syndrome (MDS), or acute myeloid leukemia (AML); and
   e. monitoring the progress of the treatment of step (d) by repeating steps (a)-(c) at predetermined time intervals, wherein a decrease over time in the expression of the truncated form of the NF-E2 protein in a blood, bone marrow, or solid tumor biopsy sample obtained from said patient subsequent to the administration of the treatment of step (d) is indicative of successful therapy.

\* \* \* \* \*